United States Patent
Miller et al.

(10) Patent No.: US 6,458,557 B1
(45) Date of Patent: Oct. 1, 2002

(54) ENHANCING GROWTH IN GRAM-POSITIVE MICROORGANISMS USING FORMATE SUPPLEMENTATION AND INACTIVATION OF FORMATE-ASSOCIATED TRANSPORT PROTEINS

(75) Inventors: Brian Miller, Burlingame; Maria Diaz-Torres, Los Gatos, both of CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/194,146

(22) PCT Filed: Nov. 19, 1998

(86) PCT No.: PCT/US98/24873
§ 371 (c)(1),
(2), (4) Date: Nov. 19, 1998

(87) PCT Pub. No.: WO99/27107
PCT Pub. Date: Jun. 3, 1999

(30) Foreign Application Priority Data

Nov. 20, 1997 (GB) ................................................ 9724627

(51) Int. Cl.[7] .................................................. C12P 1/00
(52) U.S. Cl. ...................... 435/41; 435/69.1; 435/183; 435/198; 435/201; 435/219
(58) Field of Search .............................. 435/320.1, 325, 435/252.3, 254.11, 419, 252.31, 41, 69.1, 183, 219, 198, 201

(56) References Cited

U.S. PATENT DOCUMENTS

| | | | |
|---|---|---|---|
| 3,817,837 A | 6/1974 | Rubenstein et al. | 195/103.5 |
| 3,850,752 A | 11/1974 | Schuurs et al. | 195/103.5 |
| 3,939,350 A | 2/1976 | Kronick et al. | 250/365 |
| 3,996,345 A | 12/1976 | Ullman et al. | 424/12 |
| 4,275,149 A | 6/1981 | Litman et al. | 435/7 |
| 4,277,437 A | 7/1981 | Maggio | 422/61 |
| 4,366,241 A | 12/1982 | Tom et al. | 435/7 |
| 4,816,567 A | 3/1989 | Cabilly et al. | 530/387 |

FOREIGN PATENT DOCUMENTS

| | | |
|---|---|---|
| EP | 0 299 108 A1 | 1/1989 |
| EP | 0 805 208 A1 | 11/1997 |
| WO | WO 88/06623 | 9/1988 |
| WO | WO 95/14099 | 5/1995 |
| WO | WO 98/03664 | 1/1998 |
| WO | WO 98/07867 | 2/1998 |

OTHER PUBLICATIONS

Glaser et al. Identificatioin and Isolation of a Gene Required for Nitrate Assimilation and Anaerobic Growth of *Bacillus subtilis*. J. of Bacteriology (Feb. 1995) 177(4): 1112–1115.*

Saxild et al. Genetic and physiological characterization of a formate–dependent 5'–phosphoribosyl–1–glycinamide transformylase activity in *Baillus subtilis*. Mol. Gen. Genet. (1994) 242:415–420.*

Kunst et al. The complete genome sequence of the Gram–positive bacterium *Bacillus subtilis*. Nature (Nov. 1997) 390: 249–256.*

Watson et al. Recombinant DNA (1992) Scientific American Books, pp. xiii–xiv, 99, 119–124, and 235–239.*

Ausubel et al., ed. *Current Protocols in Molecular Biology*, John Wiley & Sons, Inc. Ch. 9, 1987.

(List continued on next page.)

*Primary Examiner*—Tekchand Saidha
*Assistant Examiner*—Kathleen M. Kerr
(74) *Attorney, Agent, or Firm*—Genencor International, Inc

(57) ABSTRACT

The present invention relates to the formate transport system in gram-positive microorganisms and provides methods for the production of products in a gram-positive microorganism. The present invention also provides the nucleic acid and amino acid sequences of FTAP 1 and FTAP 2 which are associated with formate transport.

19 Claims, 30 Drawing Sheets

OTHER PUBLICATIONS

Bakhiet et al., "Studies on Transfection and Transformation of Protoplasts of *Bacillus larvae, Bacillus subtilis*, and *Bacillus popilliae*," *Applied and Environmental Microbiology*, vol. 49, No. 3, pp. 577–581, Mar., 1985.

Benton et al., "Steering λgt Recombinant Clones by Hybridization to Single Plaques in situ," *Science*, vol. 196, No. 4286, pp. 180–182, Apr. 8, 1977.

*Berger and Kimmel, "Guide to Molecular Cloning Techniques," *Methods in Enzymology*, Academic Press, San Diego, CA vol. 152, 1987.

Chang et al., "High Frequency Transformation of *Bacillus subtilis* Protoplasts by Plasmid DNA," *Molec. Gen. Genet.*, vol. 168, pp. 111–115, 1979.

Contente et al., "Marker Rescue Transformation by Linear Plasmid DNA in *Bacillus subtilis*," *Plasmid*, vol. 2, pp. 555–571, 1979.

Debarbouille, Michel et al., "The sacT Gene Regulating the sacPA Operon in *Bacillus subtilis* Shares Strong Homology with Transcriptional Antiterminators," *Journal of Bacteriology*, vol. 172, No. 7, pp. 3966–3973, Jul., 1990.

Fischer et al., "Introduction of plasmid pC194 into *Bacillus thuringiensis* by Protoplast transformation and plasmid transfer," *Archives of Microbiolog7*, vol. 139, pp. 213–217, 1984.

Fleming, Alastair et al., "Extracellular Enzyme Synthesis in a Sporulation–Deficient Strain of *Bacillus licheniformis*," *Applied and Environmental Microbiology*, vol. 61, No. 11, pp. 3775–3780, Nov., 1995.

Glaser, P. et al., "*Bacillus subtilis* genome project: cloning and sequencing of the 97 kb region from 325° to 333°," *Molecular Microbiology*, vol. 10, No. 2, pp. 371–384, 1993.

Grunstein et al., "Colony hybridization: A method for the isolation of cloned DNAs that contain a specific gene," *Proc. Nat. Acad. Sci. USA*, vol. 72, No. 10, pp. 3961–3965, Oct., 1975.

Haima, Peter et al., "Novel plasmid marker rescue transformation system for molecular cloning in *Bacillus subtilis* enabling direct selection of recombinants," *Mol. Gen. Genet.*, vol. 223, pp. 185–191, 1990.

Holubova et al., "Transfer of Liposome–Encapsulated Plasmid DNA to *Bacillus subtilis* Protoplasts and Calcium–Treated *Escherichia coli* Cells," *Folia Microbiol.*, vol. 30, pp. 97–100, 1985.

Kroll et al., "A Multifunctional Prokaryotic Protein Expression System: Overproduction, Affinity Purification, and Selective Detection," *DNA and Cell Biology*, vol. 12, No. 5, pp. 441–453, 1993.

Maddox et al., "Elevated Serum Levels in Human Pregnancy of a Molecule Immunochemically Similar to Eosinophil Granule Major Basic Protein," *J. Exp. Med.*, vol. 158, pp. 1211–1226, Oct., 1983.

Mann et al., "Transformation of *Bacillus spp.*: an Examination of the Transformation of Bacillus Protoplasts by Plasmids pUB110 and pHV33," *Current Microbiology*, vol. 13, pp. 191–195, 1986.

Mazel, Didier et al., "Genetic characterization of polypeptide deformylase, a distinctive enzyme of eubacterial translation," *The EMBO Journal*, vol. 13, No. 4 pp. 914–923, 1994.

Mazel, Didier et al., "A Survey of Polypeptide Deformylase Function Throughout the Eubacterial Lineage," *J. Mol. Biol.*, vol. 266, pp. 939–949, 1997.

McDonald et al., "Plasmid Transformation of *Bacillus sphaericus* 1593," *Journal of General Microbiology*, vol. 130, pp. 203–208, 1984.

Murray et al., "Codon usage in plant genes," *Nucleic Acids Research*, vol. 17, No. 2, pp. 477–498, 1989.

Nagy, Peter et al., "Formyltetrahydrofolate Hydrolase, a Regulatory Enzyme That Functions To Balance Pools of Tetrahydrofolate and One–Carbon Tetrahydrofolate Adducts in *Escherichia coli*," *Journal of Bacteriology*, vol. 177, No. 5, pp. 1292–1298, Mar., 1995.

Nishiyama, et al., "A novel membrane protein involved in protein translocation across the cytoplasmic membrane of *Escherichia coli*," *The EMBO Journal*, vol. 12, No. 9, pp. 3409–3415.

Nishiyama et al., "Disruption of the gene encoding p12 (SecG) reveals the direct involvement and important function of SecG in the protein translocation of *Escherichia coli* at low temperature," *The EMBO Journal*, vol. 13, No. 14, pp. 3272–3277, 1994.

Nolling, Jork et al., "Growth– and Substrate–Dependent Transcription of the Formate Dehydrogenase (fdhCAB) Operon in *Methanobacterium thermoformicicum* Z–245," *Journal of Bacteriology*, vol. 179, No. 3, pp. 899–908, Feb., 1997.

Porath, Jerker, "Immobilized Metal Ion Affinity Chromatography," *Protein Expression and Purification*, vol. 3, pp. 263–281, 1992.

Saizieu, Antoine de et al., "The trp RNA–binding attenuation protein (TRAP) regulates the steady–state levels of transcripts of the *Bacillus subtilis* folate operon," *Microbiology*, vol. 143, pp. 979–989, 1997.

Sambrook, J. et al., Molecular Cloning, A Laboratory Manual, $2^{nd}$ ed. Cold Spring Harbor Laboratory Press, Ch. 1–4, 1989.

Smith, Michael et al., "Protoplast Transformation in Coryneform Bacteria and Introduction of an α–Amylase Gene from *Bacillus amyloliquefaciens* into *Brevibacterium lactofermentum*," *Applied and Environmental Microbiology*, vol. 51, No. 3, pp. 634–639, Mar., 1988.

Sorokin, Alexei et al., "Sequence of the *Bacillus subtilis* genome region in the vicinity of the lev operon reveals two new extracytoplasmic function RNA polymerase sigma factors SigV and SigZ," *Microbiology*, vol. 143, pp. 2939–2943, 1997.

Suppmann, Bernhard et al., "Isolation and characterization of hypophosphite–resistant mutants of *Escherichia coli*: Identification of the FocA protein, encoded by the pfl operon, as a putative formate transporter," *Molecular Microbiology*, vol. 11, No. 5, pp. 965–982, 1994.

Trieu–Cuot Patrick et al., "Nucleotide sequence of the *Streptococcus faecalis* plasmid gene encoding the 3'5"–aminoglycoside phosphotransferase type III," *Gene*, vol. 23, pp. 331–341, 1983.

Vorobjeva, I.P. et al., "Transformation of *Bacillus megaterium* Protoplasts by Plasmid DNA," *FEMS Microbiology Letters* 7, pp. 261–263, 1980.

Warren, W., et al., "Increased production of peptide deformylase eliminates retention of formylmethionine in bovine somatrotropin overproduced in *Escherichia coli*," *Gene*, vol. 174, pp. 235–238, 1996.

Weinrauch et al., "Plasmid Marker Rescue Transformation Proceeds by Breakage–Reunion in *Bacillus subtilis*," *Journal of Bacteriology*, vol 169, No. 3, pp. 1205–1211, Mar., 1987.

Weinrauch et al., "Plasmid Marker Rescue Transformation in *Bacillus subtilis*," *Journal of Bacteriology*, vol. 154, No. 3, pp. 1077–1087, Jun., 1983.

Whitehead, Terence et al., "Distribution of 10–Formyltetrahydrofolate Synthetase in Eubacteria," *Journal of Bacteriology*, vol. 170, No. 2, pp. 995–997, Feb. 1988.

Database EMBL Nucleotide and Protein Sequences, XP–002105622, Nov. 18, 1997 GenBank Accession AJ002571.

Database EMBL Nucleotide and Protein Sequences, XP–002105615, Apr. 16, 1997 GenBank Accession U93874.

Database EMBL Nucleotide and Protein Sequences, PCT/US98/24873, Jul. 15, 1998 GenBank Accession O05399.

* cited by examiner

```
AGGCTAAAGCAATGGAATGTATGCACGAACTGTATATATTCTCTTTCAATATCTTATATA
         +         +         +         +         +         + 60
TCCGATTTCGTTACCTTACATACGTGCTTGACATATATAAGAGAAAGTTATAGAATATAT

CTGCTTGATATATTGTTGTATGGGTATGCATACAAGTTAGGCAGCATTCAAACGCCTGGTTT
         +         +         +         +         +         + 120
GACGAACTATAACAACATACCCATACGTATGTTCAATCCGTCGTAAGTTTGCGGACCAAA

GACACAGGTTATTTGAGTGCTGCCTTTTTTATTGCCTTTCTTGCATAACTGTGAGAAAAG
         +         +         +         +         +         + 180
CTGTGTCCAATAAACTCACGACGGAAAAAATAACGGAAAGAACGTATTGACACTCTTTTC

AAGAAGTAATGGAGGCGTTTATTATGGCTTTTTCGAAACCGGATGAAATAGCGGAAGCA
         +         +         +         +         +         + 240
TTCTTCATTACCTCCGCAAATAATACCGAAAAAGCTTTGGCCTACTTTATCGCCTTCGT

Met Ala Phe Arg Lys Pro Asp Glu Ile Ala Glu Ala
                 ─────────────── YrhG ───────────────

GCAATTGAAGCAGGGATGAAAAAAATAAAGCTCCCGTCCGTCACTGCTTGTGCTGGGG
         +         +         +         +         +         + 300
CGTTAACTTCGTCCCTACTTTTTTTATTTCGAGGGCAGGCAGTGACGAACACGACCCC

Ala Ile Glu Ala Gly Met Lys Lys Ile Lys Leu Pro Ser Leu Leu Val Leu Gly
─────────────────────────── YrhG ───────────────────────────
```

```
TTTTAGGGGGTGCATTTATCGCGCTTGGGTATTTGCTTGATATCAGGGTAATTGGCGAT
                                                            + 360
AAAAATCCGCCACGTAAATAGCGCGAACCCATAAACGAACTATAGTCCCATTAACCGCTA

Phe Leu Gly Gly Ala Leu Gly Tyr Leu Leu Asp Ile Arg Val Ile Gly Asp
                                    YrhG

CTTCCGAAAGAATGGGGGAGCCTGTCCAGTTTGATTGGTGCAGCAGTATTTCCAGTCGGC
                                                            + 420
GAAGGCTTTCTTACCCCCTCGGACAGGTCAAACTAACCACGTCGTCATAAAGGTCAGCCG

Leu Pro Lys Glu Trp Gly Ser Leu Ser Ser Leu Ile Gly Ala Ala Val Phe Pro Val Gly
                                    YrhG

CTGATCCTTGTGTCGTTCTCGCTTGGGCCTGAACTGATCACAGGCAATATGATGTCAGTTGCG
                                                            + 480
GACTAGGAACAGCAAGAGCGAACCCGGACTTGACTAGTGTCCGTTATACTACAGTCAACGC

Leu Ile Leu Val Val Leu Ala Gly Ala Glu Leu Ile Thr Gly Asn Met Met Ser Val Ala
                                    YrhG

ATGGCGTTATTTTCGAGAAAATATCAGTAAAAGAGTTAGGCGATTAACTGGGGAATCGTC
                                                            + 540
TACCGCAATAAAAGCTCTTTTATAGTCATTTTCTCAATCCGCTAATTGACCCCTTAGCAG

Met Ala Leu Phe Ser Arg Lys Ile Ser Val Lys Glu Leu Ala Ile Asn Trp Gly Ile Val
                                    YrhG
```

FIG._1A-2

```
ACAATTATGAACTTAATCGGGCGCATTGTTGTTGCTTACTTTTTCGGGCATTTGGTTGGA
     +         +         +         +         +         + 600
TGTTAATACTTGAATTAGCCGCGTAACAACGAATGAAAAAGCCCGTAAACCAACCT

Thr Ile Met Asn Leu Ile Gly Ala Leu Phe Val Ala Tyr Phe Phe Gly His Leu Val Gly
                            YrhG

TTGACTGAAACAGGTCCTTATTTAGAAAAAACGATTGCCGTTGCCCAAGGAAAGCTTGAT
     +         +         +         +         +         + 660
AACTGACTTTGTCCAGGAATAAATCTTTTTGCTAACGGCAACGGGTTCCTTTCGAACTA

Leu Thr Glu Thr Gly Pro Tyr Leu Glu Lys Thr Ile Ala Val Ala Gln Gly Lys Leu Asp
                            YrhG

ATGAGCTTTGGCAAGGTTCTCATTTCCGCCATCGGGCTGTAACTGGCTTGTATGTCTTGCA
     +         +         +         +         +         + 720
TACTCGAAACCGTTCCAAGAGTAAAGGCGGTAGCCGACATTGACCGAACATACAGAACGT

Met Ser Phe Gly Lys Val Leu Ile Ser Ala Ile Gly Cys Asn Trp Leu Val Cys Leu Ala
                            YrhG

GTGTGGCTTTCTTTTCGGGCGCCAAGACGCAGCAGGAAAAATCCTTGGCATCTGGTTCCCA
     +         +         +         +         +         + 780
CACACCGAAAGAAAAGCCGCGGTTCTGCGTCGTCCTTTTTAGGAACCGTAGACCAAGGGT

Val Trp Leu Ser Phe Gly Ala Gln Asp Ala Ala Gly Lys Ile Leu Gly Ile Trp Phe Pro
                            YrhG
```

FIG. _1B-1

```
ATCATGGCTTTTGTGGCTATCGGATTTCAGCACGTTGTCGCCAACATGTTTGTGATTCCT
----+----+----+----+----+----+----+----+----+----+----+----+ 840
TAGTACCGAAAACACCGATAGCCTAAAGTCGTGCAACAGCGGTTGTACAAACACTAAGGA

Ile Met Ala Phe Val Ala Ile Gly Phe Gln His Val Val Ala Asn Met Phe Val Ile Pro
                                          YrhG

GCTGCCATTTTTGCAGGCTCATTCACGTGGGGGCAGTTCATCGGAAACATCATTCCGGCT
----+----+----+----+----+----+----+----+----+----+----+----+ 900
CGACGGTAAAAACGTCCGAGTAAGTGCACCCCCGTCAAGTAGCCTTTGTAGTAAGGCCGA

Ala Ala Phe Ala Gly Ser Phe Thr Trp Gly Gln Phe Ile Gly Asn Ile Ile Pro Ala
                                          YrhG

TTTATCGGTAATGTCATCGGCGGAGCTGTATTTGTCGGTCTCATTTATTTATTGCATAT
----+----+----+----+----+----+----+----+----+----+----+----+ 960
AAATAGCCATTACAGTAGCCGCCTCGACATAAACAGCCAGAGTAAATAAAATAACGTATA

Phe Ile Gly Asn Val Ile Gly Gly Ala Val Phe Val Gly Leu Ile Tyr Phe Ile Ala Tyr
                                          YrhG

CATAAGAAAGACCGCTCCAGAAAAGAAATGAAGCAGGTGTCATGACCAACGGGCAAATCC
----+----+----+----+----+----+----+----+----+----+----+----+ 1020
GTATTCTTTCTGGCGAGGTCTTTTCTTTACTTCGTCCACAGTACTGGTTGCCCGTTTAGG

His Lys Lys Asp Arg Ser Arg Lys Glu Met Lys Gln Val Ser
                                          YrhG
```

FIG._1B-2

```
ATTCGATGATTGCACAATTCCGTCCATTTTTAGAAAAAGATGTTTACAAAATGGAATT
     +         +         +         +         +         +      1080
TAAGCTACTAAACGTGTTAAAGGCAGGTAAAAATCTTTTCTACAAATGTTTACCTTAA

TGGTGGATATACTTACAAAG
     +         ↑ 1100
ACCACCTATATGAATGTTTC
```

FIG._1C

```
CTTTTTCATTTACGCAAATTTTAGGTCTTGCCTGCTTACCAGTCACAATCCCGCTTATT
----+----+----+----+----+----+----+----+----+----+----+----+  60
GAAAAAGTAAATGCGTTTAAAATCCAGAACGGACGAAATGGTCAGTGTTAGGGCGAATAA

CAGATTAAGAATACGCTTTCATCATAAATCATGATAGCGTTTCGTCAACTATTTTTTA
----+----+----+----+----+----+----+----+----+----+----+----+  120
GTCTAATTCTTATGCGAAAGTAGTATTAGTACTATCGCAAAGCAGTTGATAAAAAAAT

GTAAATAGTTTGATATAACATGTAGACAAAAATTCGTAAAAATTAATTGTGAAATACTT
----+----+----+----+----+----+----+----+----+----+----+----+  180
CAATTTATCAAACTATATTGTACATCTGTTTTTAAGCATTTTTAATTAACACTTTATGAA

CACAATATCGTGCCATACTATGCTCAATCATGAAAGAAAGCAGGAAAAGACAATGGAAAC
----+----+----+----+----+----+----+----+----+----+----+----+  240
GTGTTATAGCACGGTATGATACGAGTTAGTACTTTCTTTCTTTCGTCCTTTTCTGTTACCCTTTG
                                                           Met Glu Thr
                                                            └── YwcJ ──

TCAAGCATTACAAAAGGTTGAACAGTATGCTTTGAAAAACAAAACATATTCGCTTCAAG
----+----+----+----+----+----+----+----+----+----+----+----+  300
AGTTCGTAATGTTTTCCAACTTGTCATACGAAACTTTTTGTTTTGTATAAGCGAAGTTC

Gln Ala Leu Gln Lys Val Glu Gln Tyr Ala Leu Lys Lys Gln Asn Ile Phe Ala Ser Ser
─────────────────────────────────────── YwcJ ──────────────────────────────────
```

FIG._2A-1

```
CAAAATCCGTTATGTGCTTCGGTCCATTTTGGCCAGTATATTTATTGGTTTTGGCATTAC
----+----+----+----+----+----+----+----+----+----+----+----+  360
GTTTTAGGCAATACACGAAGCCAGGTAAAACCGGTCATATAAATAACCAAAACCGTAATG

Lys Ile Arg Tyr Val Leu Arg Ser Ile Leu Ala Ser Ile Phe Ile Gly Phe Gly Ile Thr
                                    YwcJ

AGCCGCAAGCAAAAACAGGCAGCTATTTCTTTATGGCTGATTCTCCGTTTGCCTTTCCGGC
----+----+----+----+----+----+----+----+----+----+----+----+  420
TCGGCGTTCGTTTTGTCCGTCGATAAAGAAATACCGACTAAGAGGCAAACGGAAAGGCCG

Ala Ala Ser Lys Thr Gly Ser Tyr Phe Phe Met Ala Asp Ser Pro Phe Ala Phe Pro Ala
                                    YwcJ

AGCCGCTGTCACTTTCGGGGGCCGCTATTCTGATGATTGCTTACGGAGGCGGAGATTTATT
----+----+----+----+----+----+----+----+----+----+----+----+  480
TCGGCGACAGTGAAAGCCCCCGGCGATAAGACTACTAACGAATGCCTCCGCCTCTAAATAA

Ala Ala Val Thr Phe Gly Ala Ala Ile Leu Met Ile Ala Tyr Gly Gly Asp Leu Phe
                                    YwcJ

TACCGGCAACACCTTTATTTCACCTATACCGCGTCCGGAAAAAAATCAGCTGGCCGA
----+----+----+----+----+----+----+----+----+----+----+----+  540
ATGGCCGTTGTGTGGAAAATAAAGTGGATATGGCGCAGGCCTTTTTTTAGTCGACCGGCT

Thr Gly Asn Thr Phe Tyr Phe Thr Tyr Thr Ala Leu Arg Lys Lys Ile Ser Trp Arg Asp
                                    YwcJ
```

FIG._2A-2

```
CACCCTATACTTGTGGATGTCAAGCTATGCCGGCAATTTAATCGGCGCCATTCTGTTTGC
     |    |    |    |    |    |    |    |    |    |    |    |   600
GTGGGATATGAACACCTACAGTTCGATACGGCCGTTAAATTAGCCGCGGTAAGACAAACG

Thr Leu Tyr Met Ser Ser Tyr Ala Gly Asn Leu Ile Gly Ala Ile Leu Phe Ala
                                    ────────────────────────────────────
                                                    YwcJ

CATCCTGATCAGCGCGACGGGACTTTTTGAGGAGCCTTCTGTTCATTCCTTTTTGATTCA
     |    |    |    |    |    |    |    |    |    |    |    |   660
GTAGGACTAGTCGCGCTGCCCTGAAAAACTCCTCGGAAGACAAGTAAGGAAAAACTAAGT

Ile Leu Ile Ser Ala Thr Gly Leu Phe Glu Glu Pro Ser Val His Ser Phe Leu Ile His
   ─────────────────────────────────────────────────────────────────────────────────
                                                YwcJ

TTTGGCAGAGAGCACAAAATGGAGCCGGCCTTCCGAATTGTTTTTCAGAGGAATGCTGTG
     |    |    |    |    |    |    |    |    |    |    |    |   720
AAACCGTCTCTCGTGTTTTACCTCGGCCGGAAGGCTTAACAAAAGTCTCCTTACGACAC

Leu Ala Glu His Lys Met Glu Pro Pro Ala Ser Glu Leu Phe Phe Arg Gly Met Leu Cys
   ─────────────────────────────────────────────────────────────────────────────────
                                                YwcJ

CAATTGGCTTGTGTGCCTCGCCTTTTCATTCCAATGTCTCTCAAAGGGGAAGGAGCAAA
     |    |    |    |    |    |    |    |    |    |    |    |   780
GTTAACCGAACACACGGAGCGGAAAAAGTAAGGTTACAGAGAGTTTCCCCTTCCTCGTTT

Asn Trp Leu Val Cys Leu Ala Phe Phe Ile Pro Met Ser Leu Lys Gly Glu Gly Ala Lys
   ─────────────────────────────────────────────────────────────────────────────────
                                                YwcJ
```

FIG._2B-1

```
GCTTTTTACCATGATGATGCTTTTCGTTTTCTGCTTCTTATTCCGGCTTTGAACACAGCAT
                                                              840
CGAAAAATGGTACTACGAAAAGCAAAAGACGAAGAAATAAAGGCCGAAACTTGTGTCGTA

Leu Phe Thr Met Met Leu Phe Val Phe Cys Phe Phe Ile Ser Gly Phe Glu His Ser Ile
                                    YwcJ

TGCCAATATGTGCACATTCGCCATCTCGCTTTTGATCGAGCACCCTGATACAGTGACACT
                                                              900
ACGGTTATACACGTGTAAGCGGTAGAGCGAAAACTAGCTCGTGGGACTATGTCACTGTGA

Ala Asn Met Cys Thr Phe Ala Ile Ser Leu Leu Ile Glu His Pro Asp Thr Val Thr Leu
                                    YwcJ

GATGGGAGCAGTCAGAAACTTAATCCCCGTTACGCTCGGCAATCTGACCGCGGGAATAGT
                                                              960
CTACCCTCGTCAGTCTTTGAATTAGGGGCAATGCGAGCCGTTAGACTGGCGCCCTTATCA

Met Gly Ala Val Arg Asn Leu Ile Pro Val Thr Leu Gly Asn Leu Thr Ala Gly Ile Val
                                    YwcJ

TATGATGGGCTGGATGTACTACACACTGAATCCTGATCAATAAAAAACTTCCAGAGATC
                                                              1020
ATACTACCCGACCTACATGATGTGTGACTTAGGACTAGTTATTTTTTGAAGGTCTCTAG

Met Met Gly Trp Met Tyr Tyr Thr Leu Asn Pro Asp Gln
                                    YwcJ
```

FIG._2B-2

```
ACTCCCTGCAAGTCAAAGCGGGTTATTCCGAGAGATCTTGAAGACGCTGGACATGCAGCGT
                                                              1080
TGAGGGACGTTCAGTTTCGCCCAATAAGGCTCTCTAGAACTTCTGCGACCTGTACGTCGCA

GATATAGCCGGCCTCGGATT
         1100
CTATATCGGCCGGAGCCTAA
```

FIG._2C

```
CCGATGGGAACGGCTTACGGGTCTCTGGACAGGAATTGGCACCGCCGGCGGGGCGCTTATC    60
         +         +         +         +         +         +
GGCTACCCTTGCCGAATGCGCCAGACCTGTCCTTAACCGTGGCGGCCGCCCCGCGAATAG

GGCATCCTCTCTTTTACAAGGAGCAGAAAGACGCCAAACGGATCTTCTTTATCGCGTTGATT   120
         +         +         +         +         +         +
CCGTAGGAGAGAAAATGTTCCTCGTCTTTCTGCGGTTTGCCTAGAAGAATAGGCAACTAA

TTATGCTCAGCAGTTGGGTTTAAAAATTCTGTCATAAATTGATTTTTATCAAATCTTCAGT   180
         +         +         +         +         +         +
AATACGAGTCGTCAACCAAATTTTTAAGACAGTATTTAACTAAAAATAGTTTAGAAGTCA

ATAATGGATAAATAGTTTAGACTTACAAAGATAAGAGGATTATTCATGAAATCATATAT    240
         +         +         +         +         +         +
TATTACCTATTTATCAAATCTGAATGTTTCTATTCCCTAATAAGTACTTTAGTATATA

Met Lys Ser Tyr Met
                                                 YkkE
GACTCAGCGGGTTGGACGAATACCGTGACGGAAATGAGGATAAA GGTCGGCTCTTGGTCAG   300
         +         +         +         +         +         +
CTGAGTCGCCCAACCTGCTTATGGCACTGCCTTTACTCCTATTTCCAGCCGAGAACCAGTC

Thr Gln Arg Leu Asp Glu Tyr Arg Asp Gly Asn Glu Asp Lys Gly Arg Leu Leu Val Ser
                                   YkkE
```

FIG._3A-1

```
CTGCCCCGATCAGCCGGGGTATCGTCTCTGCAGTTTCCGCGTTTTATTTGAACACGGTGC
                                                            360
GACGGGGCTAGTCGGCCCCATAGCAGAGACGTCAAAGGCGCAAAAATAAACTTGTGCCACG

Cys Pro Asp Gln Pro Gly Ile Val Ser Ala Phe Leu Phe Glu His Gly Ala
                                      YkkE

CAATATTATAGAATCAAATCAATATACGACAGACCCTGAAGGCGGCCGGTTCTTCCTGAG
                                                            420
GTTATAATATCTTAGTTTAGTTATATGCTGTCTGGGACTTCCGCCGGCCAAGAAGGACTC

Asn Ile Ile Glu Ser Asn Gln Tyr Thr Thr Asp Pro Glu Gly Gly Arg Phe Phe Leu Arg
                                      YkkE

AATCGAATTCGACTGCGCAGGCATTCGTGAAAAAAAATCATCACTTCAGGCAGCGTTTGC
                                                            480
TTAGCTTAAGCTGACGCGTCCGTAAGCACTTTTTTTTAGTAGTGAAGTCCGTCGCAAACG

Ile Glu Phe Asp Cys Ala Gly Ile Arg Glu Lys Lys Ser Ser Leu Gln Ala Ala Phe Ala
                                      YkkE

CTCTGTTGCGGGAAAAATTCGACATGACATGGAGCTTAACTTTGGCGAGCGAACTGAAGCG
                                                            540
GAGACAACGCCCTTTTTAAGCTGTACTGTACCTCGAATTGAAACCGCTCGCTTGACTTCGC

Ser Val Ala Glu Lys Phe Asp Met Thr Trp Ser Leu Thr Leu Ala Ser Glu Leu Lys Arg
                                      YkkE
```

FIG._3A-2

```
TGTCGCCATTTTCGTTTCAAAGAATCTCCACTGCCTGCATGAGCTGATTTGGGAATGGCA
————————+—————————+—————————+—————————+—————————+—————————+ 600
ACAGCGGTAAAAGCAAAGTTTCTTAGAGGTGACGGACGTACTCGACTAAACCCTTACCGT

Val Ala Ile Phe Val Ser Lys Asn Leu His Cys Leu Ile Trp Glu Trp Gln
                             YkkE

AACCGGCAACCTGATGGCGGAGATCGCTGTTGTCATCAGTAACCATGAGGAAGCGGAGAGA
————————+—————————+—————————+—————————+—————————+—————————+ 660
TTGGCCGTTGGACTACCGCCTCTAGCGACAACAGTAGTCATTGGTACTCCTTCGCTCTCT

Thr Gly Asn Leu Met Ala Glu Ile Ala Val Val Ile Ser Asn His Glu Ala Arg Glu
                             YkkE

GCTGGTTGAGCGCCTGAACATTCCATTCCACTATATGAAAGCGAACAAAGACATCAGAGC
————————+—————————+—————————+—————————+—————————+—————————+ 720
CGACCAACTCGCGGACTTGTAAGGTAAGGTGATATACTTTCGCTTGTTTCTGTAGTCTCG

Leu Val Glu Arg Leu Asn Ile Pro Phe His Tyr Met Lys Ala Asn Lys Asp Ile Arg Ala
                             YkkE

GGAAGTCGAAAAGAAGCAGCTTGAACTGCTGGAGCAGTACGATGTTGATCGTGCT
————————+—————————+—————————+—————————+—————————+—————————+ 780
CCTTCAGCTTTTCTTCGTCGAACTTGACGACCTCGTCATGCTACAACTAGCACGA

Glu Val Glu Lys Lys Gln Leu Glu Leu Leu Glu Gln Tyr Asp Val Asp Val Ile Val Leu
                             YkkE
```

FIG. 3B-1

```
CGCACGCTATATGCAGATTCTAACTCCTGATTTTGTTTCGGCTCATCCGAATCGCATCAT
     +         +         +         +         +         +     840
GCGTGCGATATACGTCTAAGATTGAGGACTAAAACAAAGCCGAGTAGGCTTAGCGTAGTA
 Ala Arg Tyr Met Gln Ile Leu Thr Pro Asp Phe Val Ser Ala His Pro Asn Arg Ile Ile
                                          YkkE

CAATATCCACCATTCATTCCTGCCAGCTTTTATCGGTGCCGAATCCGTACAAACGGGCCTA
     +         +         +         +         +         +     900
GTTATAGGTGGTAAGTAAGGACGGTCGAAAATAGCCACGCTTAGGCATGTTTGCCCGGAT
 Asn Ile His His Ser Phe Leu Pro Ala Phe Ile Gly Ala Asn Pro Tyr Lys Arg Ala Tyr
                                     YkkE

CGAGCGCGGGCTGAAACTGATCGGTGCCGACATCTCATTATGTGACAAACGATCTTGATGA
     +         +         +         +         +         +     960
GCTCGCGCCCGACTTTGACTAGCCACGGCTGTAGAGTAATACACTGTTTGCTAGAACTACT
 Glu Arg Gly Val Lys Leu Ile Gly Ala Thr Ser His Tyr Val Thr Asn Asp Leu Asp Glu
                                  YkkE

AGGGCCGATCATTGAACAGGATATTAAGCGTGTGGACCACCGCGATAATGCGGAAACGCT
     +         +         +         +         +         +     1020
TCCCGGCTAGTAACTTGTCCTATAATTCGCACACCTGGTGGCGCTATTACGCCTTTGCGA
 Gly Pro Ile Ile Glu Gln Asp Ile Lys Arg Val Asp His Arg Asp Asn Ala Glu Thr Leu
                                     YkkE
```

FIG. 3B-2

```
GAAAAACATCGGAAGAACAATTGAGGCGGCAGCGTGCTTGCCCGTGCTGTGAAATGGCATTT
————————+————————+————————+————————+————————+————————+ 1080
CTTTTTGTAGCCTTCTTGTTAACTCGCGTCGACGGGCACGACACTTTACCGTAAA

Lys Asn Ile Gly Arg Thr Ile Glu Arg Ser Val Leu Ala Arg Ala Val Lys Trp His Leu
                                                YkkE

GGAAGACCGTGTCATCGTCGTTCATGAAAATAAAACAATCGTCTTTAACTAGACTGCAAGAGG
————————+————————+————————+————————+————————+————————+ 1140
CCTTCTGGCACAGTAGCAAGTACTTTTATTTTGTTAGCAGAAATTGATCTGACGTTCTCC

Glu Asp Arg Val Ile Val His Glu Asn Lys Thr Ile Val Phe Asn
                                                  YkkE

CCCGCGCAATGCGGGCTATTTTTTGATGACAAAAACCCTTGACAAGTGTCTTTTTCTTTG
————————+————————+————————+————————+————————+————————+ 1200
GGGCGCGTTACGCCCGATAAAAACTACTGTTTTTGAACTGTTCACAGAAAAAGAAAC

CATAATATATAAAAAAATCATTGAGCGTTGAAGAGGATTAGTAAGCAGACCT
————————+————————+————————+————————+————————→ 1250
GTATTATATTTTTTAGTAACTCGCAACTTCTCCTAATCATTCGTCTGGA
```

FIG._3C

```
TTGGCAGTAAAAAGGTCGTCACACATCCTGCGGAGGTTTTGGAAACACCTGCGGAAACCGTGACTGTTT
       +         +         +         +         +         +         +   70
AACCGTCATTTTTCCAGCAGTGTGTAGGACGCCTCCAAAACCTTTGTGGACGCCTTTGGCACTGACAAA

Leu Ala Val Lys Lys Val Val Thr His Pro Ala Glu Val Leu Glu Thr Pro Ala Glu Thr Val Thr Val

TTGATAAAAAGCTAAAAAAACTGCTTGATGATATGTACGACACCATGCTTGAAATGGATGGTGTCGGACT
       +         +         +         +         +         +         +  140
AACTATTTTTCGATTTTTTTGACGAACTACTATACATGCTGTGGTACGAACTTTACCTACCACAGCCTGA

Phe Asp Lys Lys Leu Lys Lys Leu Leu Asp Asp Met Tyr Asp Thr Met Leu Glu Met Asp Gly Val Gly Leu

GGCAGCGCGCAAATCGGCATTTTAAAAGAGCCGGTCGTAGAAATCGGGGATGACAGAGGGAGAATT
       +         +         +         +         +         +         +  210
CCGTCGCGCGTTTAGCCGTAAAATTTTTCTCGGCCAGCATCTTTAGCCCTACTGTCTCCCCTCTTAA

Ala Ala Pro Gln Ile Gly Ile Leu Lys Arg Ala Ala Val Glu Ile Gly Asp Asp Arg Gly Arg Ile

GATCTCGTTAATCCTGAAATTTTAGAAAAAAAGCGGCGAGCAAACCGGAATTGAAGGATGCTTGAGCTTTC
       +         +         +         +         +         +         +  280
CTAGAGCAATTAGGACTTTAAAATCTTTTTTTCGCCGCTCGTTTGGCCTTAACTTCCTACGAACTCGAAAG

Asp Leu Val Asn Pro Glu Ile Leu Glu Lys Ser Gly Glu Gln Thr Gly Ile Glu Gly Cys Leu Ser Phe
```

*FIG._4A-1*

```
CTAACGTCTATGGTGATGTCACACGTGCCGATTATGTCAAAGTGCTGCGTTTAACCGTCAGGGAAAACC
     |         |         |         |         |         |         |    350
GATTGCAGATACCACTACAGTGTGCACGGCTAATACAGTTTCACGCACGCAAATTGGCAGTCCCTTTTGG
Pro Asn Val Tyr Gly Asp Val Thr Arg Ala Asp Tyr Val Lys Val Arg Ala Phe Asn Arg Gln Gly Lys Pro

GTTCATTCTGGAAGCGCGGAGGCTTTTTAGCAAGAGCCGTGCAGCATGAAATGGACCACTTAGACGGGTGTG
     |         |         |         |         |         |         |    420
CAAGTAAGACCTTCGCGCCTCCGAAAAATCGTTCTCGGCACGTCGTACTTTACCTGGTGAATCTGCCACAC
Phe Ile Leu Glu Ala Arg Gly Phe Leu Ala Arg Ala Val Gln His Glu Met Asp His Leu Asp Gly Val
```

FIG._4A-2

```
CTGTTTACACATCTAAAAATAAGTAAATACTATACAGAAGATGAACTAGCCGGATATGGAAGGATGA
     |         |         |         |         |         |         |↑ 483
GACAAATGTAGAGATTTTATTCATTTATGATATGTCTTCTACTTGATCGCCTATACCTTCCTACT
Leu Phe Thr Ser Lys Ile Ser Lys Tyr Tyr Thr Glu Asp Glu Leu Ala Asp Met Glu Gly  •
```

FIG._4B

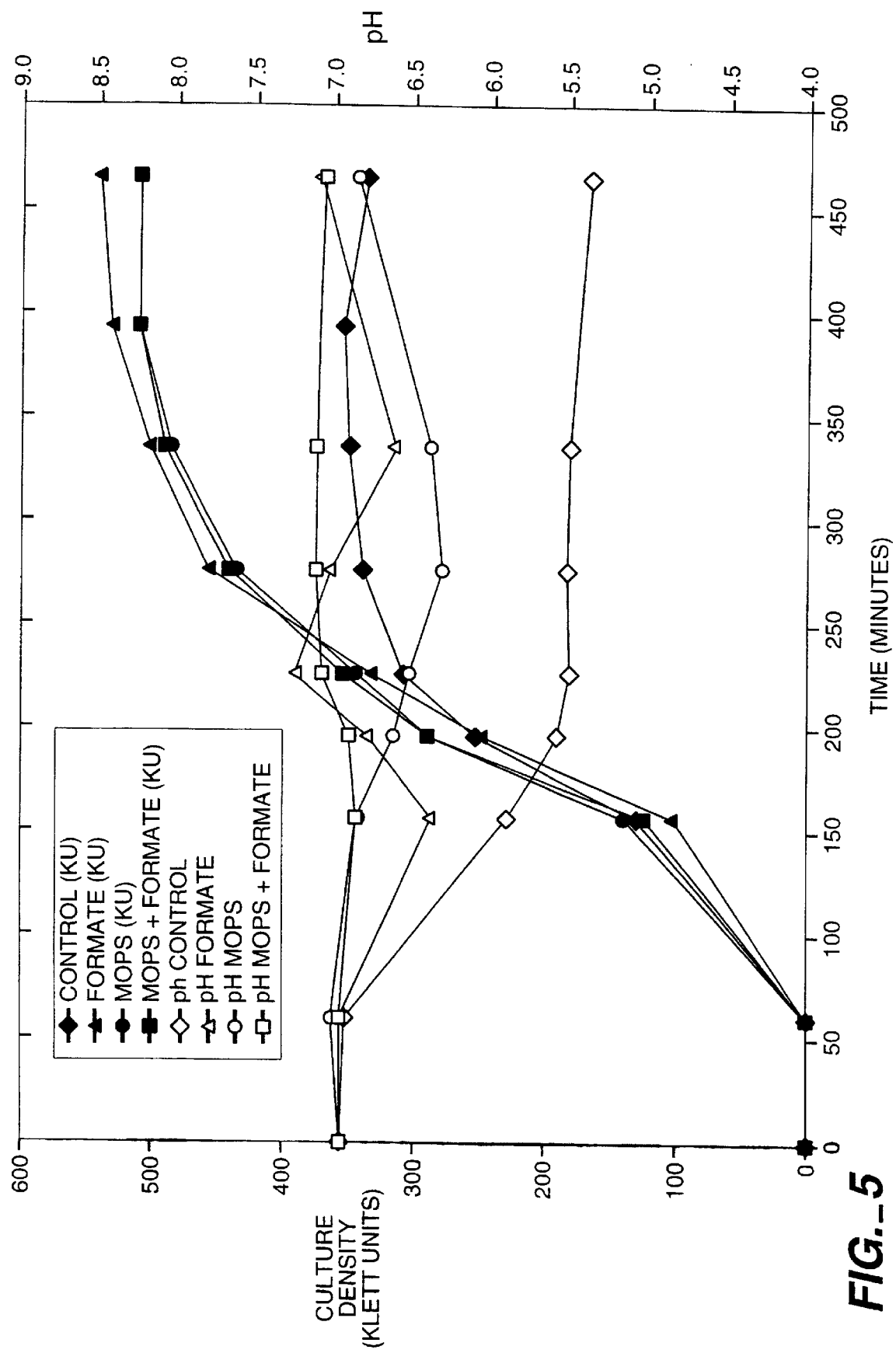
FIG._5

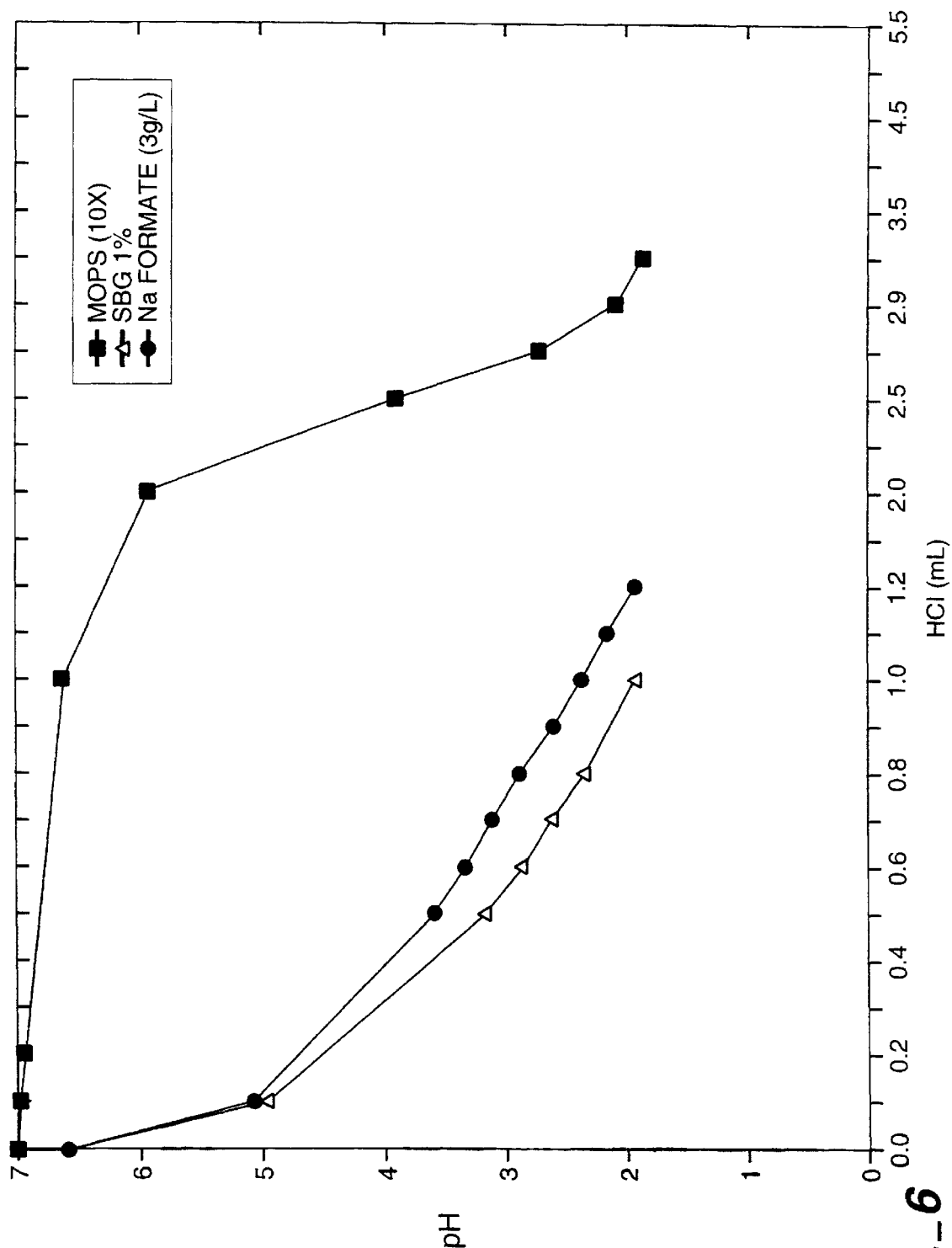
FIG._6

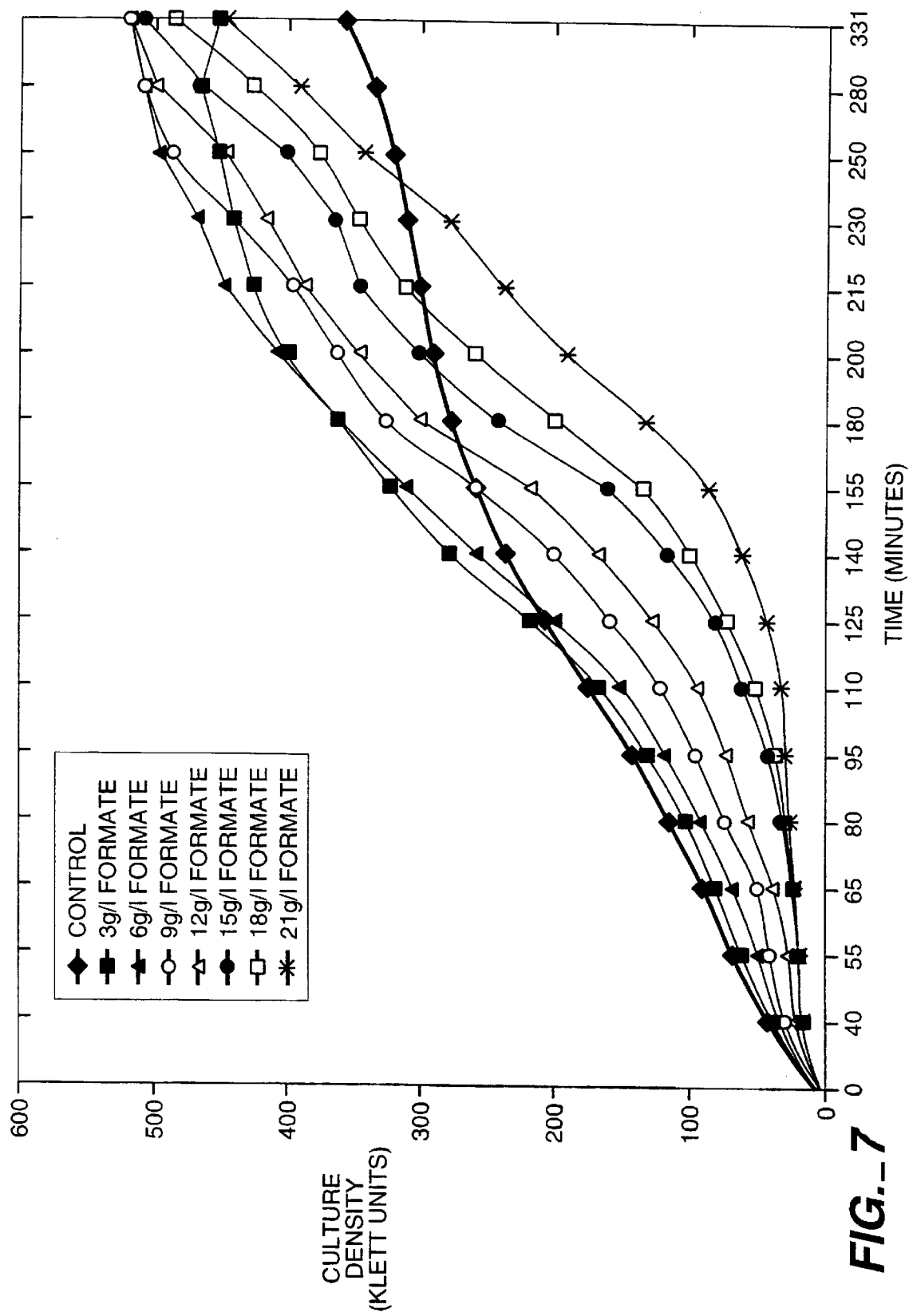
FIG._7

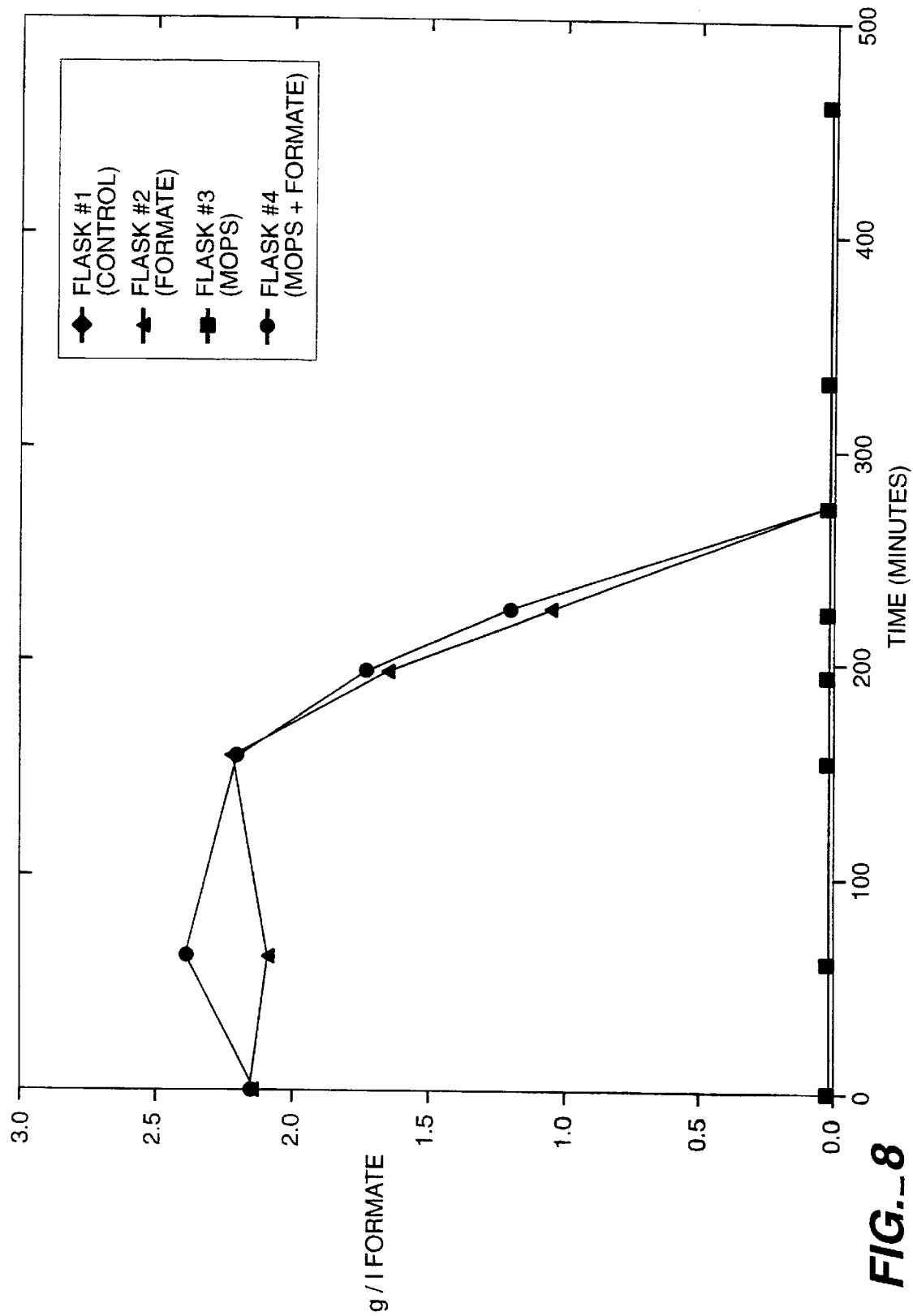
FIG._8

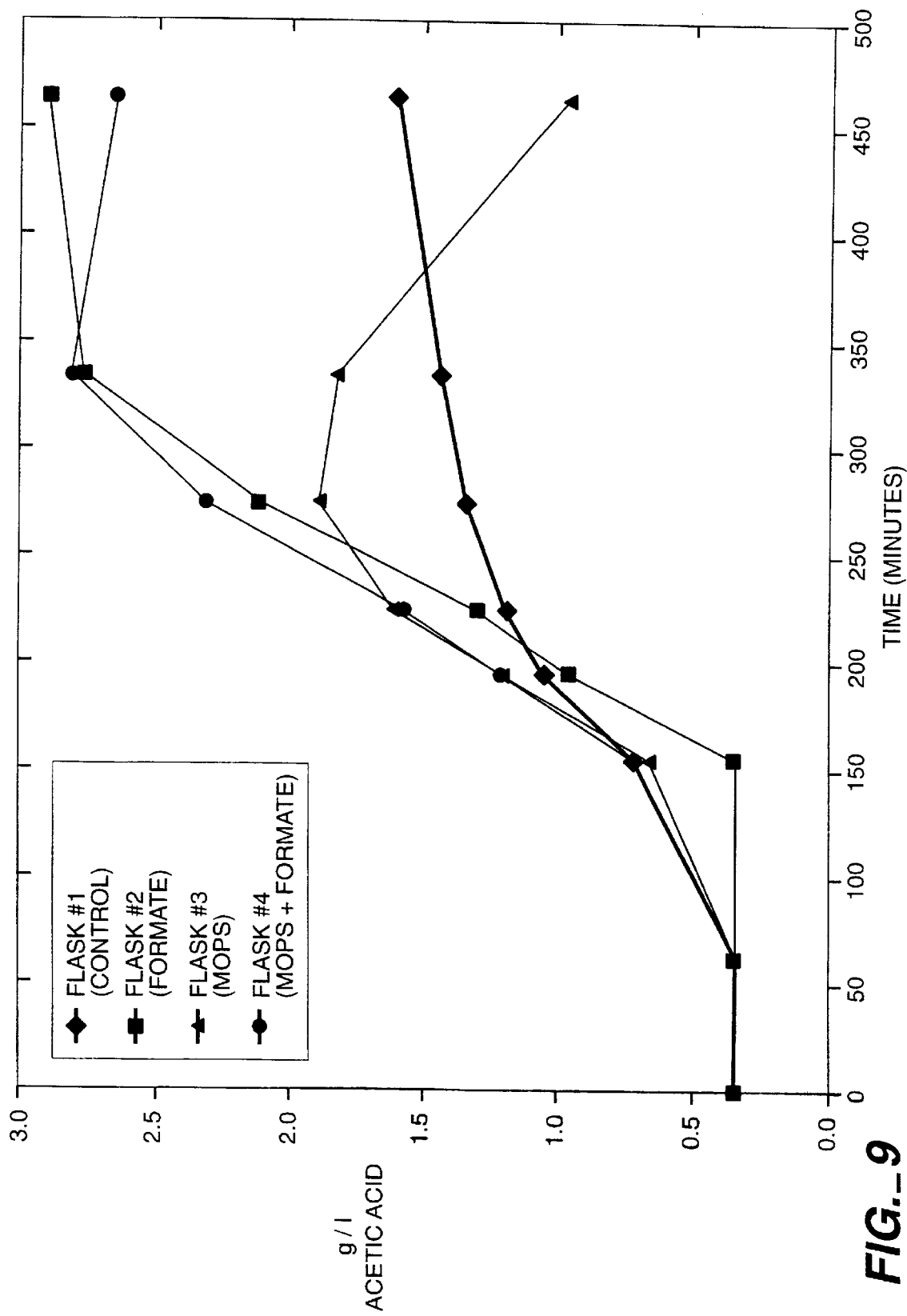
FIG._9

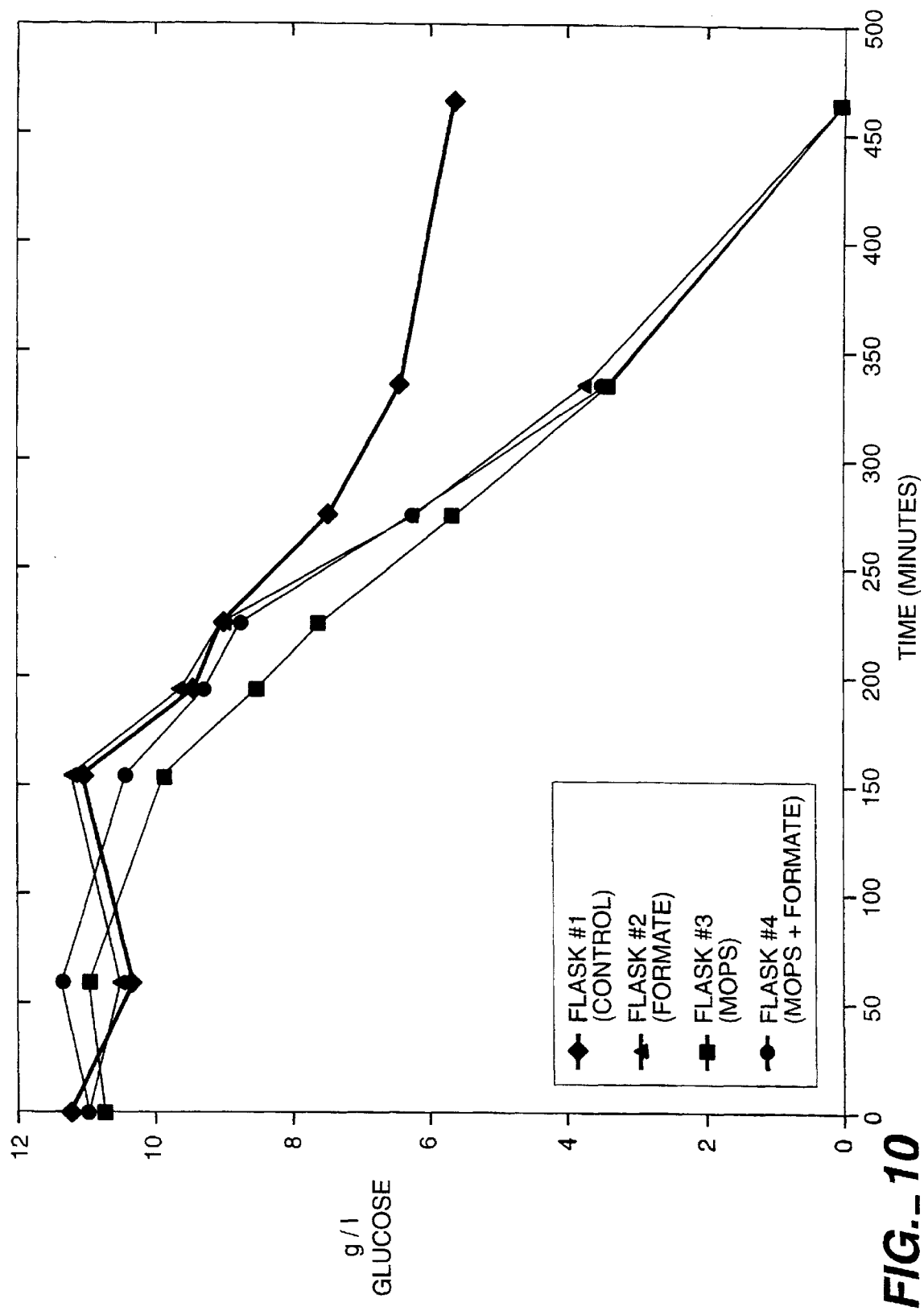
FIG._10

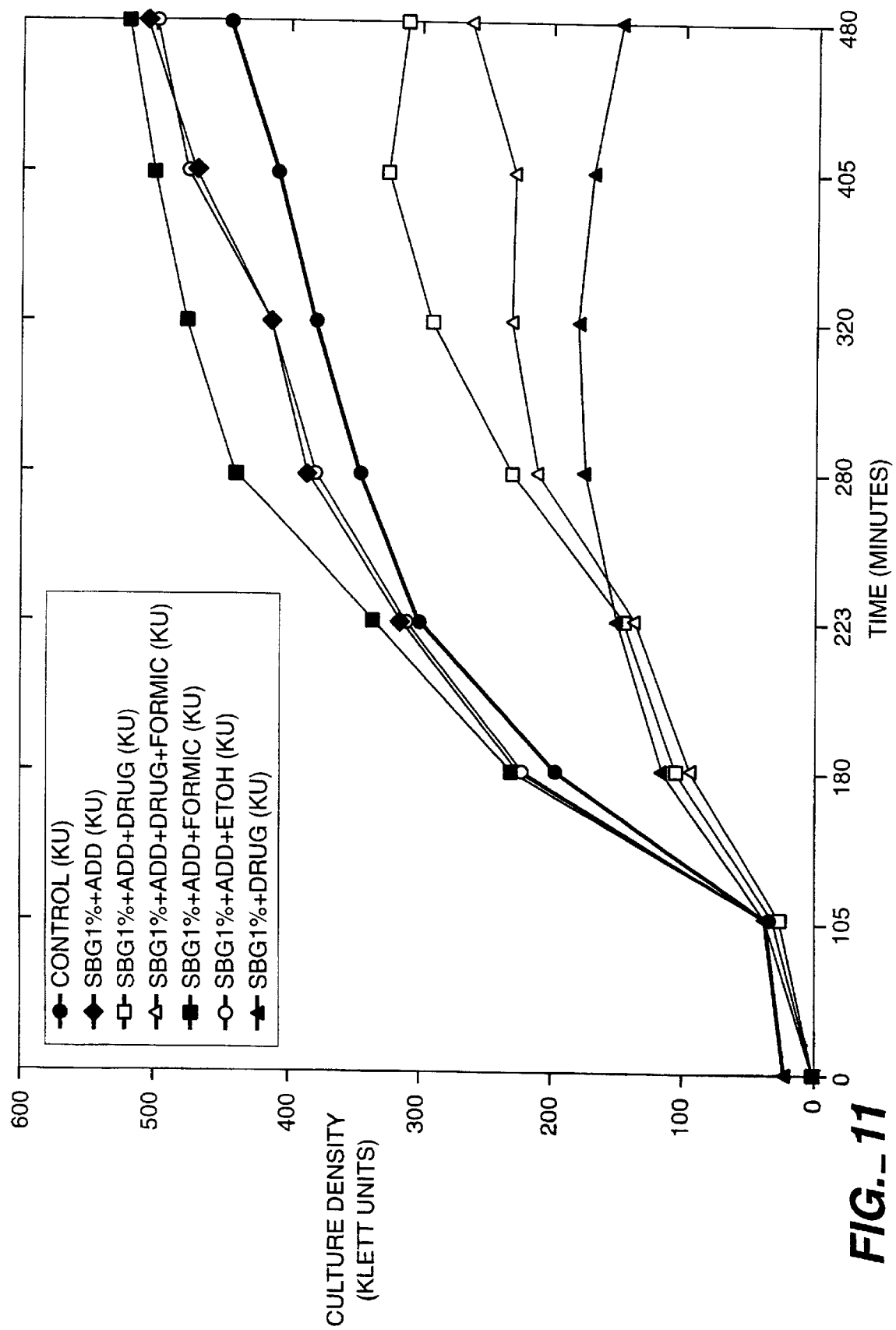
FIG._11

```
ecopflz.pl                                         MPFGMAKLVGGICFSLGLILCVVCGADLFTSTVL
                                                   :::  ::  :|: :: |||:::  |||
YRHG        VLGFLGGAFIALGYLLDIRVIGDLPKEWGSLSSLIGAAVFPVGLILVVLAGAELITGNMM
                 30            40            50            60            70            80 ecopflz.pl  -IVVAKASGRITWGQLAKNWLNVYFGNLVGALLFVLLMWLSGEYMTANGQWGLNVLQTAD
             :: :|: :: ||    :   || |:: ||| ||:|||||:|||  ||||||||||:
YRHG        SVAMALFSRKISVKELAINWGIVTIMNLIGAL-FVAYFFGHLVGLTETGPYLEKTIAVAQ
                 90           100           110           120           130           140 ecopflz.pl  HKVHHTFIEAVCLGILANLMVCLAVWMSYSGRSLMDKAFIMVLPVAMFVASGFEHSIANM
             |:  ||  : ||| |:|:|||||| |:  |  :||||||:|||:|||:||||| |||:
YRHG        GKLDMSFGKVLISAIGCNWLVCLAVWLSFGAQDAAGKILGIWFPIMAFVAIGFQHVVANM
                150           160           170           180           190           200 ecopflz.pl  FMIPMGIVIRDFASPEFWTAVGSAPENFSHLTVMNFITDNLIPVTIGNIIGGGLLVGLTY
             |:: |:|| |  |  :  |  :           ||  ||:|  ||| :|||:||||:
YRHG        FVIPAAI----FAGSFTW---GQ----------FI-GNIIPAFIGNVIGGAVFVGLIY
                210                 220           230                   240 ecopflz.pl  WVIYLRENDHH
             :: |  |:::
YRHG        FIAYHKKDRSRKEMKQVS
                250           260
```

FIG._12

```
ecopflz.p1                                                       MPFGMAKLVGGICFSLGLILCV7CGADLFTS
                                                                  |::  :::::  ::    ::  ::|||  ::
YWCJ        VLRSILASIFIGFGITAASKTGSYFFFMADSPFAFP--AAAVTFGAAILMIAYGGGDLFTG
                  10        20        30        40        50        60        70        80        90
                                                                              10        20        30 ecopflz.p1  TVLIVVAKA-SGRITWGQLAKNWLNVYFGNLVGALLFVLLMWLSGEYMTANGQWGLNVLQ
            :::  : ::::   :: |:::: : ::: :::   : |::: ::::::  : :::  ::  :   ::
YWCJ        NTFYFTYTALRKKISWRDTLYLWMSSYAGNLIGAILFAILISATGLFEEPSVHSFL--IH
                  90        100       110       120       130       140
                  40        50        60        70        80        90 ecopflz.p1  TADHKVHHTFIEAVCLGILANLMVCLAVWMSYSGRSLMDKAFIMVLPVAMFVASGFEHSI
            |:  : :::   :::: :::::  — :::  :   ::: :::  ::|::  :::::::
YWCJ        LAEHKMEPPASELFFRGMLCNWLVCLAFFIPMSLKGEGAKLFTMMLFVFCFFISGFEHSI
                  150       160       170       180       190       200
                  100       110       120       130       140       150 ecopflz.p1  ANMFMIPMGIVIRDFASPEFWTAVGSAPENFSHLTVMNFITDNLIPVTIGNIIGGGLLVG
            |||  :    :::  :::  — :::             ::::: :::  :::  :::::::
YWCJ        ANMCTFAISLLIEH---PDTVTLMGAV---------RNLIPVTLGNLTAGIVMMG
                  210       220                       230       240
                  160       170       180       190       200       210 ecopflz.p1  LTYWVIYLRENDHH
            :: :: :|  :|:
YWCJ        ---WMYYTLNPDQ
                  220
                  250
```

FIG._13

```
                         10              20              30              40
puru.pl YKKE           MHSLQRKVLRTICPDQKGLIARITNICYKHELNIVQNNEFV-DHRTG
                         10              20              30         40

50              60              70              80              90             100
puru.pl        MKSYMTQRLDEYRDGNEDKGRLLVSCPDQPGIVSAVSAFLFEHGANIIESNQYTTDPEGG
                ||  ::   | |::  : ::   ||| |   ||::|| | ::   :|   :  |
YKKE           RFFMRTELE--GIFND-STLLADLDSALPEGSVR-ELNPAGR-RRIVILVTKEAHCLGDL
                         50              60          70           80              90             100

110             120             130             140             150             160
puru.pl        RFFLRIEFDCAGIREKKSSLQAAFASVAEKFDMTWSLTLASELKRVAIFVSKNLHCLHEL
                || |  |     :  :  ::|: :    : | :   |::|    :|     ::    |
YKKE           LMKANYGGLDVEIAAVIGNHDTLRSLVERFDIPFELVSHEGLTRNEHDQKMADAIDAYQP
                        110             120             130             140             150             160

170             180             190             200             210             220
puru.pl        IWEWQTGNLMAEIAVVISNHEEARELVERLNIPFHYMKANKDIRAEVEKKQLELLEQYDV
                :  :  :    :|:|:   :  : |    |::|  ::  :|    |||   :|:  ||
YKKE           DYVVLAKYMRVLTPEFVARFPNKIINIHHSFLPAFIGARPYHQAYERGVKIIGATAHYVN
                        170             180             190             200             210             220

230             240             250             260             270             280
puru.pl        DVIVLARYMQILTPDFVSAHPNRIINIHHSFLPAFIGANPYKRAYERGVKLIGATSHYVT
                : :  |    :|  |  |: :  : ::    |  :     |   ::    ::: :::
YKKE           DNLDEGPIIMQDVIHVDHTYTAEDMMRAGRDVEKNVLSRALYKVLAQRVFVYGNRTIIL
                        230             240             250             260             270             280

290             300
puru.pl        NDLDEGPIIEQDIKRVDHRDNAETLKNIGRTIERSVLARAVKWHLEDRVIVHENKTIVFN
YKKE                        
                        290             300
```

FIG._14

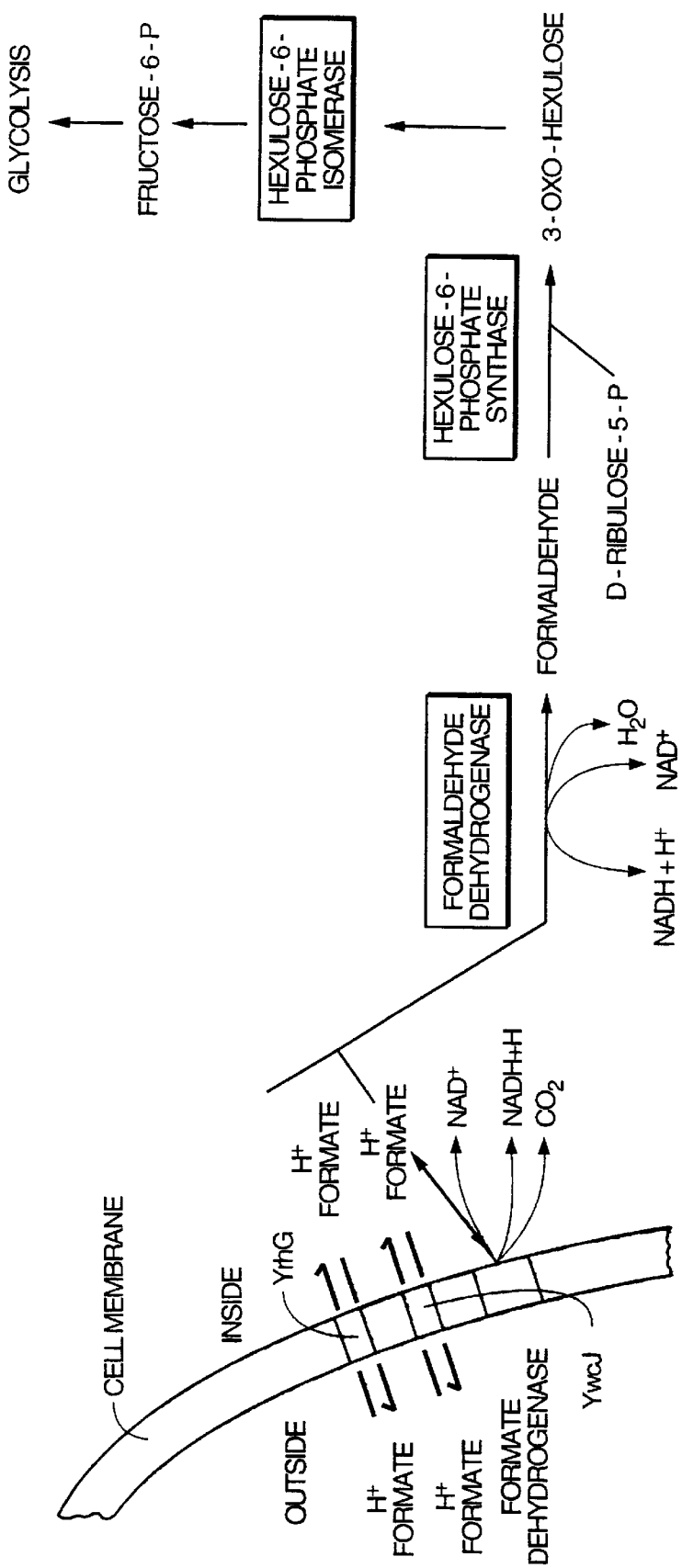
FIG._15B
FIG._15

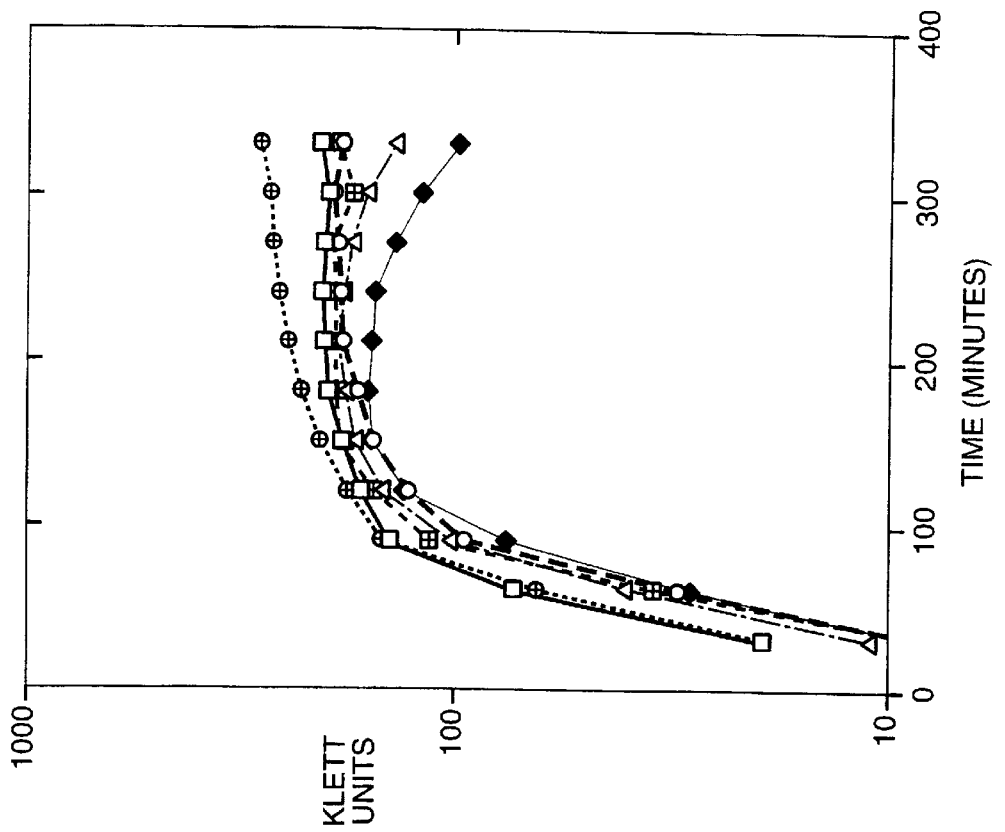
FIG._17
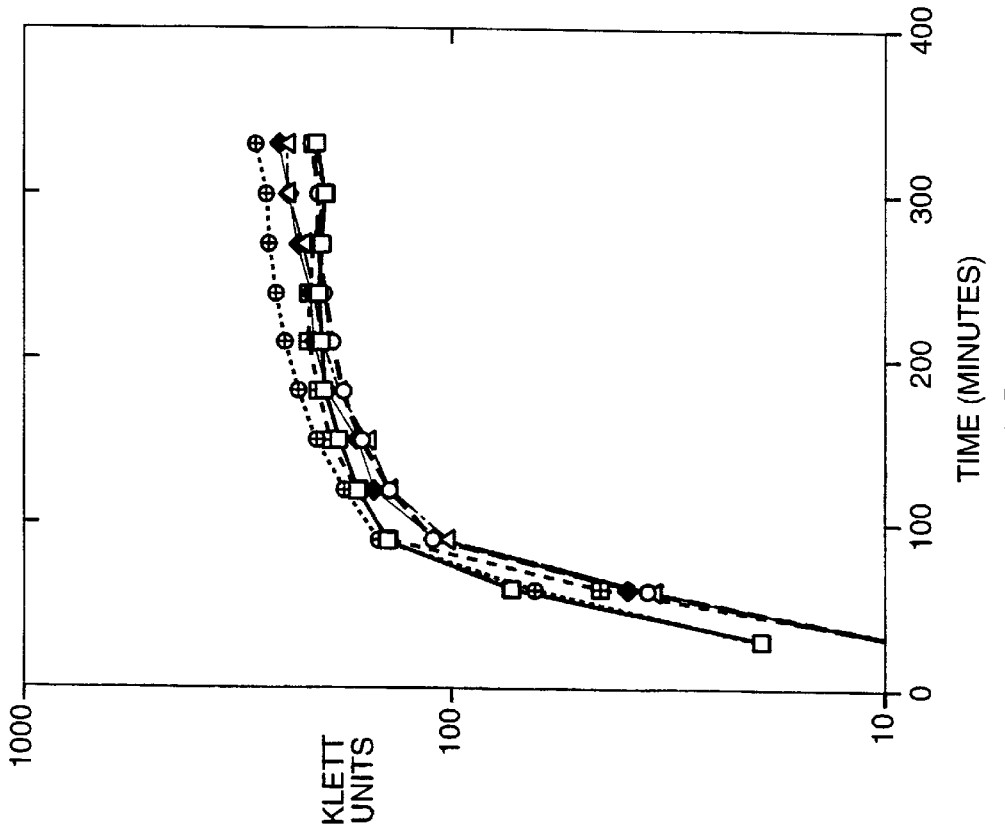
FIG._16

SEQUENCE LISTING

<160> NUMBER OF SEQ ID NOS: 14

<210> SEQ ID NO 1
<211> LENGTH: 801
<212> TYPE: DNA
<213> ORGANISM: Bacillus

<400> SEQUENCE: 1

```
atggctttc gaaaaccgga tgaaatagcg gaagcagcaa ttgaagcagg gatgaaaaaa      60
ataaagctcc cgctgccgtc actgcttgtg ctggggtttt taggcggtgc atttatcgcg    120
cttgggtatt tgcttgatat cagggtaatt ggcgatcttc cgaaagaatg ggggagcctg    180
tccagtttga ttggtgcagc agtatttcca gtcggcctga tccttgtcgt tctcgctggc    240
gctgaactga tcacaggcaa tatgatgtca gttgcgatgg cgttattttc gagaaaaata    300
tcagtaaaag agttagcgat taactgggga atcgtcacaa ttatgaactt aatcggcgca    360
ttgtttgttg cttactttt cgggcatttg gttggattga ctgaaacagg tccttattta    420
gaaaaaacga ttgccgttgc ccaaggaaag cttgatatga gctttggcaa ggttctcatt    480
tccgccatcg gctgtaactg gcttgtatgt cttgcagtgt ggctttcttt cggcgcccaa    540
gacgcagcag gaaaaatcct tggcatctgg ttcccaatca tggcttttgt ggctatcgga    600
tttcagcacg ttgtcgccaa catgtttgtg attcctgctg ccattttgc aggctcattc    660
acgtgggggc agttcatcgg aaacatcatt ccggcttta tcggtaatgt catcggcgga    720
gctgtatttg tcggtctcat ttatttatt gcatatcata agaaagaccg ctccagaaaa    780
gaaatgaagc aggtgtcatg a                                              801
```

<210> SEQ ID NO 2
<211> LENGTH: 266
<212> TYPE: PRT
<213> ORGANISM: Bacillus

<400> SEQUENCE: 2

```
Met Ala Phe Arg Lys Pro Asp Glu Ile Ala Glu Ala Ala Ile Glu Ala
 1               5                  10                  15

Gly Met Lys Lys Ile Lys Leu Pro Leu Pro Ser Leu Leu Val Leu Gly
             20                  25                  30

Phe Leu Gly Gly Ala Phe Ile Ala Leu Gly Tyr Leu Leu Asp Ile Arg
         35                  40                  45

Val Ile Gly Asp Leu Pro Lys Glu Trp Gly Ser Leu Ser Ser Leu Ile
     50                  55                  60

Gly Ala Ala Val Phe Pro Val Gly Leu Ile Leu Val Val Leu Ala Gly
 65                  70                  75                  80

Ala Glu Leu Ile Thr Gly Asn Met Met Ser Val Ala Met Ala Leu Phe
                 85                  90                  95

Ser Arg Lys Ile Ser Val Lys Leu Ala Ile Asn Trp Gly Ile Val
            100                 105                 110

Thr Ile Met Asn Leu Ile Gly Ala Leu Phe Val Ala Tyr Phe Phe Gly
        115                 120                 125

His Leu Val Gly Leu Thr Glu Thr Gly Pro Tyr Leu Glu Lys Thr Ile
    130                 135                 140

Ala Val Ala Gln Gly Lys Leu Asp Met Ser Phe Gly Lys Val Leu Ile
145                 150                 155                 160

Ser Ala Ile Gly Cys Asn Trp Leu Val Cys Leu Ala Val Trp Leu Ser
```

```
                165                 170                 175
Phe Gly Ala Gln Asp Ala Ala Gly Lys Ile Leu Gly Ile Trp Phe Pro
            180                 185                 190

Ile Met Ala Phe Val Ala Ile Gly Phe Gln His Val Val Ala Asn Met
        195                 200                 205

Phe Val Ile Pro Ala Ala Ile Phe Ala Gly Ser Phe Thr Trp Gly Gln
    210                 215                 220

Phe Ile Gly Asn Ile Ile Pro Ala Phe Ile Gly Asn Val Ile Gly Gly
225                 230                 235                 240

Ala Val Phe Val Gly Leu Ile Tyr Phe Ile Ala Tyr His Lys Lys Asp
                245                 250                 255

Arg Ser Arg Lys Glu Met Lys Gln Val Ser
            260                 265
```

<210> SEQ ID NO 3
<211> LENGTH: 771
<212> TYPE: DNA
<213> ORGANISM: Bacillus

<400> SEQUENCE: 3

```
atggaaactc aagcattaca aaaggttgaa cagtatgctt tgaaaaaaca aaacatattc    60
gcttcaagca aaatccgtta tgtgcttcgg tccattttgg ccagtatatt tattggtttt   120
ggcattacag ccgcaagcaa aacaggcagc tatttcttta tggctgattc tccgtttgcc   180
tttccggcag ccgctgtcac tttcggggcc gctattctga tgattgctta cggaggcgga   240
gatttattta ccggcaacac ctttatttc acctataccg cgctccggaa aaaaatcagc   300
tggcgcgaca ccctatactt gtggatgtca agctatgccg gcaatttaat cggcgccatt   360
ctgtttgcca tcctgatcag cgcgacggga cttttttgagg agccttctgt tcattccttt   420
ttgattcatt tggcagagca caaaatggag ccgccggctt ccgaattgtt tttcagagga   480
atgctgtgca attggcttgt gtgcctcgcc ttttttcattc caatgtctct caaaggggaa   540
ggagcaaagc ttttttaccat gatgcttttc gttttctgct tctttatttc cggctttgaa   600
cacagcattg ccaatatgtg cacattcgcc atctcgcttt tgatcgagca ccctgataca   660
gtgacactga tgggagcagt cagaaactta atccccgtta cgctcggcaa tctgaccgcg   720
ggaatagtta tgatgggctg gatgtactac acactgaatc ctgatcaata a           771
```

<210> SEQ ID NO 4
<211> LENGTH: 256
<212> TYPE: PRT
<213> ORGANISM: Bacillus

<400> SEQUENCE: 4

```
Met Glu Thr Gln Ala Leu Gln Lys Val Glu Gln Tyr Ala Leu Lys Lys
1               5                   10                  15

Gln Asn Ile Phe Ala Ser Ser Lys Ile Arg Tyr Val Leu Arg Ser Ile
            20                  25                  30

Leu Ala Ser Ile Phe Ile Gly Phe Gly Ile Thr Ala Ala Ser Lys Thr
        35                  40                  45

Gly Ser Tyr Phe Phe Met Ala Asp Ser Pro Ala Phe Pro Ala Ala
    50                  55                  60

Ala Val Thr Phe Gly Ala Ala Ile Leu Met Ile Ala Tyr Gly Gly Gly
65                  70                  75                  80

Asp Leu Phe Thr Gly Asn Thr Phe Tyr Phe Thr Tyr Thr Ala Leu Arg
                85                  90                  95
```

Lys Lys Ile Ser Trp Arg Asp Thr Leu Tyr Leu Trp Met Ser Ser Tyr
            100                 105                 110

Ala Gly Asn Leu Ile Gly Ala Ile Leu Phe Ala Ile Leu Ile Ser Ala
        115                 120                 125

Thr Gly Leu Phe Glu Glu Pro Ser Val His Ser Phe Leu Ile His Leu
    130                 135                 140

Ala Glu His Lys Met Glu Pro Pro Ala Ser Glu Leu Phe Phe Arg Gly
145                 150                 155                 160

Met Leu Cys Asn Trp Leu Val Cys Leu Ala Phe Phe Ile Pro Met Ser
                165                 170                 175

Leu Lys Gly Glu Gly Ala Lys Leu Phe Thr Met Met Leu Phe Val Phe
            180                 185                 190

Cys Phe Phe Ile Ser Gly Phe Glu His Ser Ile Ala Asn Met Cys Thr
        195                 200                 205

Phe Ala Ile Ser Leu Leu Ile Glu His Pro Asp Thr Val Thr Leu Met
    210                 215                 220

Gly Ala Val Arg Asn Leu Ile Pro Val Thr Leu Gly Asn Leu Thr Ala
225                 230                 235                 240

Gly Ile Val Met Met Gly Trp Met Tyr Tyr Thr Leu Asn Pro Asp Gln
                245                 250                 255

<210> SEQ ID NO 5
<211> LENGTH: 903
<212> TYPE: DNA
<213> ORGANISM: Bacillus

<400> SEQUENCE: 5

| | |
|---|---:|
| atgaaatcat atatgactca gcggttggac gaataccgtg acggaaatga ggataaaggt | 60 |
| cggctcttgg tcagctgccc cgatcagccg ggtatcgtct ctgcagtttc cgcgttttta | 120 |
| tttgaacacg gtgccaatat tatagaatca aatcaatata cgacagaccc tgaaggcggc | 180 |
| cggttcttcc tgagaatcga attcgactgc gcaggcattc gtgaaaaaaa atcatcactt | 240 |
| caggcagcgt ttgcctctgt tgcggaaaaa ttcgacatga catggagctt aactttggcg | 300 |
| agcgaactga agcgtgtcgc catttttcgtt tcaaagaatc tccactgcct gcatgagctg | 360 |
| atttgggaat ggcaaaccgg caacctgatg gcggagatcg ctgttgtcat cagtaaccat | 420 |
| gaggaagcga gagagctggt tgagcgcctg aacattccat tccactatat gaaagcgaac | 480 |
| aaagacatca gagcggaagt cgaaaagaag cagcttgaac tgctggagca gtacgatgtt | 540 |
| gatgtgatcg tgctcgcacg ctatatgcag attctaactc ctgattttgt ttcggctcat | 600 |
| ccgaatcgca tcatcaatat ccaccattca ttcctgccag ctttttatcgg tgcgaatccg | 660 |
| tacaaacggg cctacgagcg cggcgtgaaa ctgatcggtg cgacatctca ttatgtgaca | 720 |
| aacgatcttg atgaagggcc gatcattgaa caggatatta gcgtgtggaa ccaccgcgat | 780 |
| aatgcggaaa cgctgaaaaa catcggaaga acaattgagc gcagcgtgct tgcccgtgct | 840 |
| gtgaaatggc atttggaaga ccgtgtcatc gttcatgaaa ataaaacaat cgtctttaac | 900 |
| tag | 903 |

<210> SEQ ID NO 6
<211> LENGTH: 300
<212> TYPE: PRT
<213> ORGANISM: Bacillus

<400> SEQUENCE: 6

-continued

Met Lys Ser Tyr Met Thr Gln Arg Leu Asp Glu Tyr Arg Asp Gly Asn
1               5                   10                  15

Glu Asp Lys Gly Arg Leu Leu Val Ser Cys Pro Asp Gln Pro Gly Ile
                20                  25                  30

Val Ser Ala Val Ser Ala Phe Leu Phe Glu His Gly Ala Asn Ile Ile
            35                  40                  45

Glu Ser Asn Gln Tyr Thr Thr Asp Pro Glu Gly Gly Arg Phe Phe Leu
    50                  55                  60

Arg Ile Glu Phe Asp Cys Ala Gly Ile Arg Glu Lys Lys Ser Ser Leu
65                  70                  75                  80

Gln Ala Ala Phe Ala Ser Val Ala Glu Lys Phe Asp Met Thr Trp Ser
                85                  90                  95

Leu Thr Leu Ala Ser Glu Leu Lys Arg Val Ala Ile Phe Val Ser Lys
            100                 105                 110

Asn Leu His Cys Leu His Glu Leu Ile Trp Glu Trp Gln Thr Gly Asn
                115                 120                 125

Leu Met Ala Glu Ile Ala Val Val Ile Ser Asn His Glu Glu Ala Arg
            130                 135                 140

Glu Leu Val Glu Arg Leu Asn Ile Pro Phe His Tyr Met Lys Ala Asn
145                 150                 155                 160

Lys Asp Ile Arg Ala Glu Val Glu Lys Lys Gln Leu Glu Leu Leu Glu
                165                 170                 175

Gln Tyr Asp Val Asp Val Ile Val Leu Ala Arg Tyr Met Gln Ile Leu
            180                 185                 190

Thr Pro Asp Phe Val Ser Ala His Pro Asn Arg Ile Ile Asn Ile His
            195                 200                 205

His Ser Phe Leu Pro Ala Phe Ile Gly Ala Asn Pro Tyr Lys Arg Ala
210                 215                 220

Tyr Glu Arg Gly Val Lys Leu Ile Gly Ala Thr Ser His Tyr Val Thr
225                 230                 235                 240

Asn Asp Leu Asp Glu Gly Pro Ile Ile Glu Gln Asp Ile Lys Arg Val
            245                 250                 255

Asp His Arg Asp Asn Ala Glu Thr Leu Lys Asn Ile Gly Arg Thr Ile
            260                 265                 270

Glu Arg Ser Val Leu Ala Arg Ala Val Lys Trp His Leu Glu Asp Arg
            275                 280                 285

Val Ile Val His Glu Asn Lys Thr Ile Val Phe Asn
            290                 295                 300

<210> SEQ ID NO 7
<211> LENGTH: 483
<212> TYPE: DNA
<213> ORGANISM: Bacillus

<400> SEQUENCE: 7
ttggcagtaa aaaaggtcgt cacacatcct gcggaggttt tggaaacacc tgcggaaacc      60
gtgactgttt ttgataaaaa gctaaaaaaa ctgcttgatg atatgtacga caccatgctt     120
gaaatggatg gtgtcggact ggcagcgccg caaatcggca tttttaaaag agcggccgtc     180
gtagaaatcg gggatgacag agggagaatt gatctcgtta atcctgaaat tttagaaaaa     240
agcggcgagc aaaccggaat tgaaggatgc ttgagctttc ctaacgtcta tggtgatgtc     300
acacgtgccg attatgtcaa agtgcgtgcg tttaaccgtc agggaaaacc gttcattctg     360
gaagcgcgag gcttttttagc aagagccgtg cagcatgaaa tggaccactt agacggtgtg     420

```
ctgtttacat ctaaaataag taaatactat acagaagatg aactagcgga tatggaagga      480
tga                                                                    483
```

<210> SEQ ID NO 8
<211> LENGTH: 160
<212> TYPE: PRT
<213> ORGANISM: Bacillus

<400> SEQUENCE: 8

```
Leu Ala Val Lys Lys Val Val Thr His Pro Ala Glu Val Leu Glu Thr
  1               5                  10                  15

Pro Ala Glu Thr Val Thr Val Phe Asp Lys Leu Lys Lys Leu Leu
                 20                  25                  30

Asp Asp Met Tyr Asp Thr Met Leu Glu Met Asp Gly Val Gly Leu Ala
             35                  40                  45

Ala Pro Gln Ile Gly Ile Leu Lys Arg Ala Ala Val Glu Ile Gly
         50                  55                  60

Asp Asp Arg Gly Arg Ile Asp Leu Val Asn Pro Glu Ile Leu Glu Lys
 65                  70                  75                  80

Ser Gly Glu Gln Thr Gly Ile Glu Gly Cys Leu Ser Phe Pro Asn Val
                 85                  90                  95

Tyr Gly Asp Val Thr Arg Ala Asp Tyr Val Lys Val Arg Ala Phe Asn
                100                 105                 110

Arg Gln Gly Lys Pro Phe Ile Leu Glu Ala Arg Gly Phe Leu Ala Arg
            115                 120                 125

Ala Val Gln His Glu Met Asp His Leu Asp Gly Val Leu Phe Thr Ser
        130                 135                 140

Lys Ile Ser Lys Tyr Tyr Thr Glu Asp Glu Leu Ala Asp Met Glu Gly
145                 150                 155                 160
```

<210> SEQ ID NO 9
<211> LENGTH: 224
<212> TYPE: PRT
<213> ORGANISM: E. coli

<400> SEQUENCE: 9

```
Met Pro Phe Gly Met Ala Lys Leu Val Gly Gly Ile Cys Phe Ser Leu
  1               5                  10                  15

Gly Leu Ile Leu Cys Val Val Cys Gly Ala Asp Leu Phe Thr Ser Thr
                 20                  25                  30

Val Leu Ile Val Val Ala Lys Ala Ser Gly Arg Ile Thr Trp Gly Gln
             35                  40                  45

Leu Ala Lys Asn Trp Leu Asn Val Tyr Phe Gly Asn Leu Val Gly Ala
         50                  55                  60

Leu Leu Phe Val Leu Leu Met Trp Leu Ser Gly Glu Tyr Met Thr Ala
 65                  70                  75                  80

Asn Gly Gln Trp Gly Leu Asn Val Leu Gln Thr Ala Asp His Lys Val
                 85                  90                  95

His His Thr Phe Ile Glu Ala Val Cys Leu Gly Ile Leu Ala Asn Leu
                100                 105                 110

Met Val Cys Leu Ala Val Trp Met Ser Tyr Ser Gly Arg Ser Leu Met
            115                 120                 125

Asp Lys Ala Phe Ile Met Val Leu Pro Val Ala Met Phe Val Ala Ser
        130                 135                 140

Gly Phe Glu His Ser Ile Ala Asn Met Phe Met Ile Pro Met Gly Ile
145                 150                 155                 160
```

```
Val Ile Arg Asp Phe Ala Ser Pro Glu Phe Trp Thr Ala Val Gly Ser
                165                 170                 175

Ala Pro Glu Asn Phe Ser His Leu Thr Val Met Asn Phe Ile Thr Asp
            180                 185                 190

Asn Leu Ile Pro Val Thr Ile Gly Asn Ile Ile Gly Gly Gly Leu Leu
            195                 200                 205

Val Gly Leu Thr Tyr Trp Val Ile Tyr Leu Arg Glu Asn Asp His His
210                 215                 220
```

<210> SEQ ID NO 10
<211> LENGTH: 280
<212> TYPE: PRT
<213> ORGANISM: E. coli

<400> SEQUENCE: 10

```
Met His Ser Leu Gln Arg Lys Val Leu Arg Thr Ile Cys Pro Asp Gln
1               5                   10                  15

Lys Gly Leu Ile Ala Arg Ile Thr Asn Ile Cys Tyr Lys His Glu Leu
            20                  25                  30

Asn Ile Val Gln Asn Asn Glu Phe Val Asp His Arg Thr Gly Arg Phe
            35                  40                  45

Phe Met Arg Thr Glu Leu Glu Gly Ile Phe Asn Asp Ser Thr Leu Leu
    50                  55                  60

Ala Asp Leu Asp Ser Ala Leu Pro Glu Gly Ser Val Arg Glu Leu Asn
65                  70                  75                  80

Pro Ala Gly Arg Arg Ile Val Ile Leu Val Thr Lys Glu Ala His
                85                  90                  95

Cys Leu Gly Asp Leu Leu Met Lys Ala Asn Tyr Gly Gly Leu Asp Val
                100                 105                 110

Glu Ile Ala Ala Val Ile Gly Asn His Asp Thr Leu Arg Ser Leu Val
            115                 120                 125

Glu Arg Phe Asp Ile Pro Phe Glu Leu Val Ser His Glu Gly Leu Thr
    130                 135                 140

Arg Asn Glu His Asp Gln Lys Met Ala Asp Ala Ile Asp Ala Tyr Gln
145                 150                 155                 160

Pro Asp Tyr Val Val Leu Ala Lys Tyr Met Arg Val Leu Thr Pro Glu
                165                 170                 175

Phe Val Ala Arg Phe Pro Asn Lys Ile Ile Asn Ile His His Ser Phe
            180                 185                 190

Leu Pro Ala Phe Ile Gly Ala Arg Pro Tyr His Gln Ala Tyr Glu Arg
            195                 200                 205

Gly Val Lys Ile Ile Gly Ala Thr Ala His Tyr Val Asn Asp Asn Leu
    210                 215                 220

Asp Glu Gly Pro Ile Ile Met Gln Asp Val Ile His Val Asp His Thr
225                 230                 235                 240

Tyr Thr Ala Glu Asp Met Met Arg Ala Gly Arg Asp Val Glu Lys Asn
                245                 250                 255

Val Leu Ser Arg Ala Leu Tyr Lys Val Leu Ala Gln Arg Val Phe Val
            260                 265                 270

Tyr Gly Asn Arg Thr Ile Ile Leu
    275                 280
```

<210> SEQ ID NO 11
<211> LENGTH: 39
<212> TYPE: DNA

```
-continued

<213> ORGANISM: Bacillus

<400> SEQUENCE: 11
gcgcgcggat ccgtaattgg cgatcttccg aaagaatgg                    39

<210> SEQ ID NO 12
<211> LENGTH: 38
<212> TYPE: DNA
<213> ORGANISM: Bacillus

<400> SEQUENCE: 12
gcgcgcctgc aggggaacca gatgccaagg atttttcc                     38

<210> SEQ ID NO 13
<211> LENGTH: 34
<212> TYPE: DNA
<213> ORGANISM: Bacillus

<400> SEQUENCE: 13
gcgcgcggat ccttggtttt ggcattacag ccgc                         34

<210> SEQ ID NO 14
<211> LENGTH: 38
<212> TYPE: DNA
<213> ORGANISM: Bacillus

<400> SEQUENCE: 14
gcgcgcctgc agagggtgct cgatcaaaag cgagatgg                     38
```

ENHANCING GROWTH IN GRAM-POSITIVE MICROORGANISMS USING FORMATE SUPPLEMENTATION AND INACTIVATION OF FORMATE-ASSOCIATED TRANSPORT PROTEINS

FIELD OF THE INVENTION

The present invention relates to the field of molecular biology and in particular to the identification of molecules involved in formate transport and utilization in Bacillus. The present invention also provides methods for increasing the yields of polypeptides produced in Bacillus.

INTRODUCTION

Gram-positive microorganisms, such as Bacillus, have been used for large-scale industrial fermentation due, in part, to their ability to secrete their fermentation products into the culture media. Secreted proteins are exported across a cell membrane and a cell wall, and then are subsequently released into the external media. It is advantageous to produce proteins of interest in gram-positive microorganisms since exported proteins usually maintain their native conformation.

Suppmann et al. (1994, Molecular Microbiology vol. 11(5), pg. 965–982) describe a putative formate transporter in a gram-negative microorganism, E. coli. Nagy et al. (1995, Journal of Bacteriology, vol: 177, pg. 1292) describe a formyltetrahydrofolate hydrolase in E. coli. Mazel et al (1997, J. Mol. Biol. 266:939–949) describe a polypeptide deformylase function in Eubacterial lineage. Little is known, however, about the uptake and utilization of formate in gram-positive microorganisms used in large scale fermentation methods for the production of heterologous proteins.

Gene products which may be associated with formate utilization have been identified in Bacillus. An operon for the production of the co-enzyme tetrahydrofolate (THF) was disclosed by de Siazieu (1997, Microbiology 143:979–989). It is also known that a 10-formyltetrahydrofolate synthetase (ligase) activity and a 5,10-methylenetetrahydrofolate dehydrogenase have been shown to exist in B. subtilis (Whitehead et al., 1988, Bacteriology 170:995–997) and Saxild et al. (1994, Mol. Gen. Genet. 242:415–420) have identified a 5'-phosphoribosyl-1-glycinamide (GAR) transforylase which catalyses a one carbon transfer reaction in purine biosynthesis. This enzyme, the product of the purT locus, was found to be dependent on formate added-either to the growth medium or to in vitro assays using cell-free extracts.

There remains a need in the art to optimize grapositive expression systems so that production of products in these systems can be increased.

SUMMARY OF THE INVENTION

Prior to the present invention, very little was known about formate transport, utilization or cycling in gram-positive microorganisms. While studying the effect of different additives on the growth of a gram-positive microorganism, Bacillus, in shake flask, a growth enhancement phenomenon was observed when sodium formate was added to the medium. Also, in the absence of exogenous formate, the phenomenon of endogenous formic acid production during gram-.positive microorganism fermentation was observed.

The present invention is therefore based, in part, upon the modification(s) in gram-positive microorganism growth observed in the presence of endogenous or exogenous sodium formate. The present invention is also based upon the evidence presented herein that formate is transported into Bacillus by a symport transport mechanism. Accordingly, the present invention provides a method for modifying the growth of gram-positive microorganisms comprising modifying formate transport in the gram-positive microorganism.

The present invention is also based, in part, upon the identification and characterization of four Bacillus proteins found encoded by genomic nucleic acid sequences of Bacillus subtilis which appear to be associated with the formate transport, utilization and cycling: formate transport associated protein 1 (FTAP1) and formate transport associated protein 2 (and FTAP2) which have about 35% and 30% identity, respectively, with the E. coli protein. FocA, a formate channel protein; Bacillus subtilis PurU, which has about 48% identity at the amino acid level with PurU of E. coli, a N10-formytetrahydrofolate hydrolase which is involved in the cycling of tetrahydrofolate and formyl tetrahydrofolate, and a formylmethionine deformylase (FMD), which has about 40% similarity to a formylmethionine deformylase (YkrB).

The present invention is further based upon data which shows that in the presence of exogenous formate, a Bacillus cell cultured in shake flask and having an interruption of the gene encoding FTAP1 exhibits about a 50% decrease in the growth enhancement normally seen in the presence of exogenous formate. In the presence of exogenous formate, a Bacillus cell cultured in shake flask and having an interruption of the gene encoding FTAP 2 grows more slowly and the density of the culture declines over time. Thus, it appears that FTAP 1 and FTAP 2 are associated with formate transport and utilization in Bacillus.

Therefore, modulating the expression of molecules involved in formate transport, utilization and cycling, e.g., FTAP 1, FTAP 2, PurU, and FMD either individually or in combination with each other or other associated molecules, provides a means for regulating the levels of formate production in gram-positive microorganisms. It may be desirable to increase the expression of such molecules, decrease the expression of such molecules, or regulate the expression of such molecules, i.e., provide a means for expressing such molecules during a defined time in cell growth, depending upon the type of gram-positive microorganism and culture conditions desired.

Accordingly, the present invention provides a method for increasing the production of a product in a gram-positive microorganism comprising the steps of obtaining a microorganism capable of expressing the product and comprising nucleic acid encoding either one or both of i) formate transport associated protein 1 (FTAP 1) and ii) formate transport associated protein 2 (FTAP 2); and culturing said microorganism in the presence of formate and under conditions suitable for expression of said product. The product includes naturally occurring products obtainable from a gram-positive microorganism, such as anti-microbial compounds, antibiotics, antigens, antibodies, surfactant, chemical products and enzymes, as well as products, such as proteins and polypeptides, which are encoded by recombinantly introduced nucleic acid.

In one aspect, the product is a recombinant protein. In one embodiment, the recombinant protein is homologous to said gram-positive microorganism and in another embodiment, the recombinant protein is heterologous to said gram-positive microorganism. In one aspect of the present invention, the gram-positive organism is a Bacillus and in yet another embodiment, the Bacillus includes *B. subtilis, B. licheniformis, B. lentus, B. brevis, B. stearothermophilus, B. alkalophilus, B. amyloliquefaciens, B. coagulans, B. circulans, B. lautus* and *Bacillus thunringiensis.*

In one aspect of the present invention, the recombinant protein includes hormones, enzymes, growth factor and cytokine and in another, the enzyme includes protease, lipase, amylase, pullulanase, cellulase, glucose isomerase, laccase and a protein disulfide isomerase.

Under large scale Bacillus fermentation conditions performed in the absence of exogenous formate, an excess of endogenous formate or formate "spillover" has been observed in the culture media. Therefor, it may be desirable to delete, mutate or otherwise interrupt the genes encoding FTAP 1 and 2 in order to maintain appropriate endogenous formate levels. Accordingly, the present invention provides a method for producing a product in a gram-positive microorganism comprising the steps of obtaining a gram-positive microorganism capable of expressing said product said microorganism having a mutation in the nucleic acid encoding either one or both of FTAP 1 and FTAP 2 said mutation resulting in inhibition of production by said microorganism of the FTAP 1 and/or FTAP 2 activity; and b) culturing said microorganism under conditions suitable for expression of said product.

Furthermore, based upon the overall amino acid sequence homology of Bacillus PurU with *E. coli* PurU, it appears that Bacillus PurU plays a role in formate transport by acting as an $N^{10}$-formyltetrahydrofolate hydrolase. Saxild et al (1994, Mol. Gen. Genet 242:415–420) speculate that, *B. subtilis* can produce formate via the deformilation of N10-formyl-THFA and of N-formyl-methionine. Accordingly, under growth conditions where excess endogenous formate appears to be spilling outside the normal formate transport pathway, it may be desirable to delete, mutate or otherwise interrupt the gene encoding PurU from the gram-positive microorganism cell in order to reduce the hydrolysis of N10-formyltetrahydrofolate, thereby increasing the formate remaining in the cell. It may also be desirable to increase expression of PurU under certain conditions of cell growth. Furthermore, as illustrated infra, expression of PurU may also be regulated metabolically through the addition of glycine or methionine into the culture media.

Accordingly, the present invention provides a method for producing a product in a gram-positive microorganism comprising obtaining a gram-positive microorganism capable of expressing the product and further comprising a mutation in the nucleic acid encoding PurU, said mutation resulting in inhibition of production by said microorganism of PurU activity; and culturing said microorganism under conditions suitable for expression of said product.

Based upon the overall sequence homology with Bacillus Def, it appears that gram-positive FMD plays a role in modifying initiating methionines. Therefore, modifying the expression of FMD in a gram positive host cell under large scale fermentation conditions may be desirable. Accordingly, the present invention provides a method for increasing the production of a product in a gram positive microorganism which comprises the steps of obtaining a gram-positive microorganism capable of expressing said product; b) modifying the expression of FMD in said microorganism; and c) culturing said microorganism under conditions suitable for expression of said product.

The present invention also provides expression vectors and gram-positive microorganims comprising isolated nucleic acid encoding FTAP 1 and/or 2 and/or PurU and/or FMD. The present invention also provides gram-positive microorganisms having a deletion or mutation of part or all of the nucleic acid encoding FTAP 1 and/or 2 and/or PurU and/or FMD.

The present invention also provides a method for the detection of *B. subtilis* FTAP 1, FTAP 2, PurU or FMD polynucleotide homologs which comprises hybridizing part or all of a nucleic acid sequence of *B. subtilis* FTAP 1, FTAP 2, PurU or FMD with gram-positive microorganism nucleic acid of either genomic or cDNA origin.

BRIEF DESCRIPTION OF THE FIGURES

FIGS. 1A–1C show the nucleic acid (SEQ ID NO: 1) and amino acid (SEQ ID NO: 2) sequence of FTAP 1 (YRHG).

FIGS. 2A–2C show the nucleic, acid (SEQ ID NO: 3) and amino acid sequence (SEQ ID NO: 4) of FTAP 2 (YWCJ).

FIGS. 3A–3C shows the nucleic (SEQ ID NO: 5) and amino acid (SEQ ID NO: 6) of PurU (YKKE).

FIGS. 4A and 4B show the nucleic acid (SEQ ID NO: 7) amino acid sequence (SEQ ID NO: 8) of FMD (Def).

FIG. 5 shows the comparison of growth and pH over time of *Bacillus subtilis* (BG125) cultures grown in SBG 1% (as described in Material and Methods herein) with the addition or absence of MOPS buffer and 3 g/l of sodium formate.

FIG. 6 shows changes in pH with the sequential addition of HCl on SBG1%, SBG1% and 80 mM MOPS, and 3 g/l formate and SBG 1%.

FIG. 7 shows the comparison of growth over time of *Bacillus subtilis* (BG125) cultures of SBG1% with the absence or addition of formate at increasing concentrations.

FIG. 8 shows the uptake of formate by cultures in FIG. 5 measured by HPLC as described in Material and Methods.

FIG. 9 shows the production of acetic acid by cultures in FIG. 5 over time measured by HPLC as described in Material and Methods.

FIG. 10 shows the uptake of glucose by cultures in FIG. 5 measured by HPLC as described in Material and Methods.

FIG. 11 shows the effect of trimethaprim addition on the growth of *Bacillus subtilis* in SBG 1% with additives and formate as indicated. Trimethaprim (Drug) was added at Klett 25 where indicated.

FIG. 12 illustrates an amino acid alignment of FTAP1, (SEQ ID NO: 2) (YRHG) with EcopFlz.p1 (which comprises *E. coli* FocA) (SEQ ID NO: 9).

FIG. 13 illustrates an amino acid alignment of FTAP2, (SEQ ID NO: 4) (YWCJ) with EcopFlz.p1 (SEQ ID NO: 9).

FIG. 14 illustrates an amino acid alignment of *E. coli* PurU (SEQ ID NO: 10) (puru.p1) with *B. subtilis* PurU (SEQ ID NO: 6) (YKKE).

FIGS. 15A and 15B illustrate schematic representation of molecules associated with formate transport, utilization and cycling in gram-positive microorganisms.

FIG. 16 illustrates the effect of the interruption (int.) of yrhG gene on the cell growth of BG125. Cells containing the gene interruption were grown in 1% SBG containing 3 g/l formate and kanamycin as indicated. Growth was determined as described in Material and Methods. Control (—∥—), Formate - - -⊕- - -), yrhG int. (---0---), yrhG int. +formate (----∆---), yrhG in.+Kan (---⊞---), yrhG int. +formate +Kan (---·♦---).

FIG. 17 illustrates the effect of the interruption (int.) of ywcJ gene on the cell growth of BG125. Cells containing: the gene interruption were grown in 1% SBG containing 3g/l formate and kanamycin as indicated. Growth was determined as described in Material and Methods. Control (—□—), Formate (---⊕---), ywcJ int. (---0---), ywxJ int. +formate (---Δ----), ywcj in. +Kan (---⊞---) ywcJ int. +formate +Kan (---◆---).

DETAILED DESCRIPTION OF THE INVENTION

Definitions

Figure 15A:
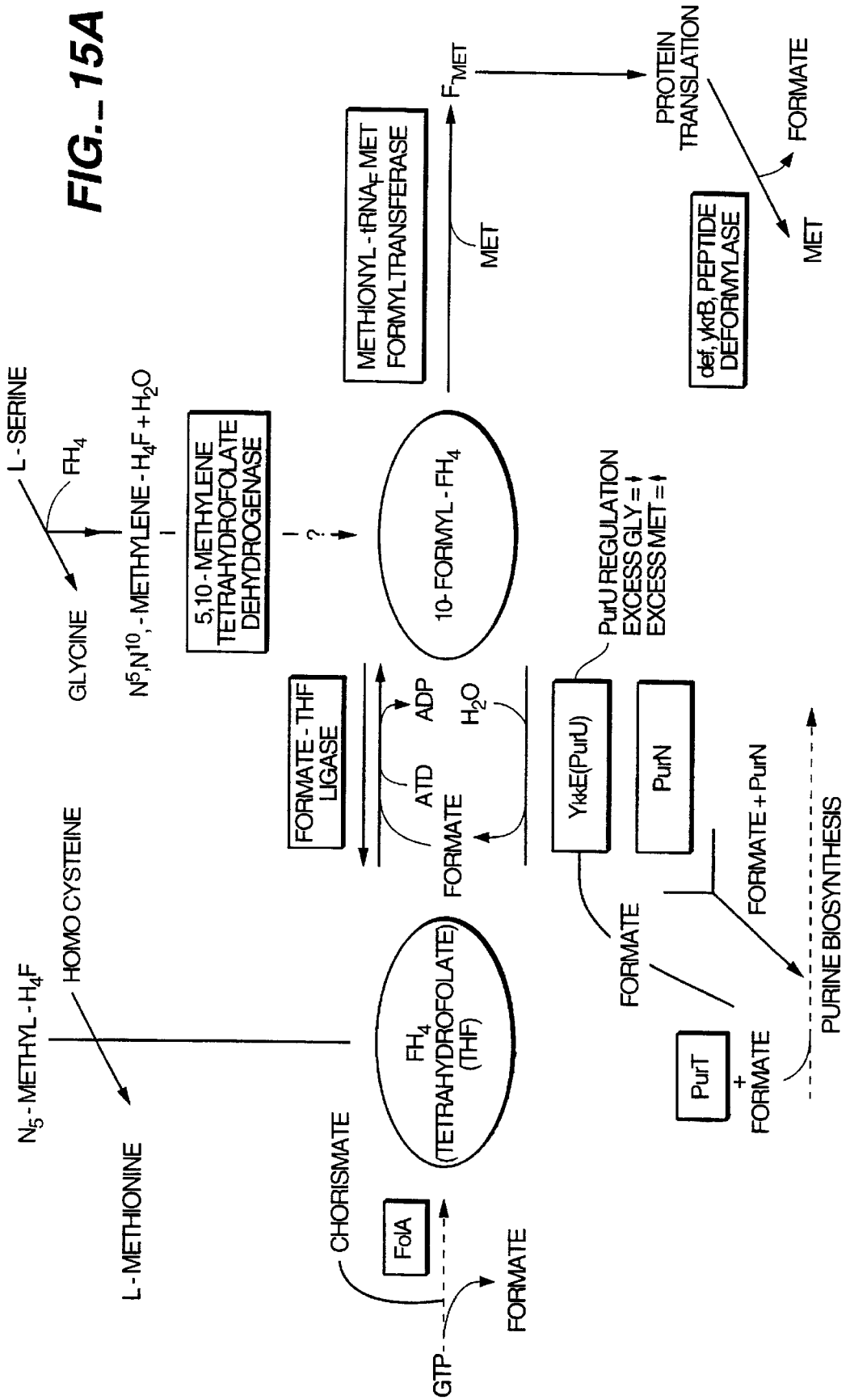

As used herein, the genus Bacillus includes all members known to those of skill in the art, including but not limited to *B. subtilis, B. licheniformis, B. lentus, B. brevis, B. stearothermophilus, S. alkalophilus, B. amyloliquefaciens, B. coagulans, B. ciculans, B. lautus* and *B. thunngiensis*.

The present invention encompasses FTAP 1, FTAP 2, PurU and FMD from gram positive organisms. In a preferred embodiment, the gram-positive organism is a Bacillus. In another preferred embodiment, the gram-positive organism is Bacillus subtilis. As used herein, "*B. subtilis* FTAP 1, FTAP 2, PurU and FMD" refers to the amino acid sequences shown in FIGS. 1, 2, 3 and 4, respectively and designated as YRHG, YWCJ, YKKE and DeF, respectively. The present invention encompasses amino acid homologs of the *B. subtilis* amino acid sequences of FTAP 1, FTAP 2, PurU and FMD, i.e., variations of the amino acid sequences disclosed in FIGS. 1, 2, 3 and 4, that retain functional capabilities and are referred to herein as, FTAP 1, FTAP 2, PurU and FMD.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof. A "polynucleotide homolog" as used herein refers to a gram-positive microorganism polynucleotide that has at least 80%, at least 85%, at least 90% and at least 95% identity to *B. subtilis* FTAP 1, FTAP 2, PurU or FMD, or which is capable of hybridizing to *B. subtilis* FTAP 1 and 2, PurU or FMD under conditions of high stringency.

The terms "isolated" or "purified" as used herein refer to a nucleic acid or protein or peptide that is removed from at least one component with which it is naturally associated, In the present invention, an isolated nucleic acid can include a vector comprising the nucleic acid.

As used herein, the term "product" refers to any naturally occurring or recombinantly introduced product obtainable from the gram-positive microorganism, e.g. protein, polypeptide, peptide, chemical and includes but is not limited to anti-microbial compounds, antibiotics, antigens, antibodies, surfactant, chemical products and enzymes. A recombinant protein is one which is encoded by nucleic acid which has been introduced into the microorganism. The nucleic acid can be introduced, on an expression vector having signals capable of expressing the protein encoded by the introduced nucleic acid or the nucleic acid can be integrated into the microorganism chromosome. The recombinant protein may be heterologous to the miooganism or homologous to the microorganism. As used herein, the term "heterologous protein" refers to a protein or polypeptide that does not naturally occur in a gram-positive host cell. Examples of heterologous proteins include enzymes such as hydrolases including proteases, cellulases, amylases, carbohydrases, and lipases; isomerases such as racemases, epimerases, tautomerases, or mutases; transferases, kinases and phophatases. The heterologous gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrases such as amylases and glucoamylases, cellulases, oxidases and lipases. The gene of interest may be a naturally occurring gene, a mutated gene or a synthetic gene.

The term "homologous protein" refers to a protein or polypeptide native or naturally occurring in a gram-positive host cell. The invention includes host cells producing the homologous protein via recombinant DNA technology. The present invention encompasses a gram-positive host cell having a deletion or interruption of the nucleic acid encoding the naturally occurring homologous protein, such as a protease, and having nucleic acid encoding the homologous protein re-introduced in a recombinant form. In another embodiment, the host cell produces the homologous protein.

It is well understood in the art that formate may exist in a variety of ionization states depending upon the surrounding media, if in solution, or out of solution from which they are prepared if in solid form. The use of a term, such as, for example, formic acid, to designate such molecules is intended to include all ionization states of the organic molecule referred to. Thus, for example, both "formic acid" and "formate" refer to the same moiety, and are not intended to specify particular ionization states.

DESCRIPTION OF THE PREFERRED EMBODIMENTS

I. Bacillus Formate Transport

A growth enhancement phenomenon observed when sodium formate was added to shake flask cultures of *Bacillus subtilis* revealed information on the mechanism of formate transport into the cell. Total cell density was much higher and the culture was able to maintain its growth rate for a longer period of time. The growth enhancement of formate was correlated with the prevention of the normal drop in pH to below 6.0 during growth in 1% SBG medium. Concentrations of sodium formate ranging from 3 g/l (44 mM) to 21 g/l (308 mM) produced a similar effect for overall growth enhancement. However, while 3 g/l sodium formate caused a only a slight lag in initial growth rate, the lag became more pronounced within creasing concentrations of formate. Growth of *B. subtilis* in 1% SBG was accompanied by the production of acetate, the likely cause of the normal pH drop and the fall in growth rate. Experiments with MOPS buffer showed that the growth enhancement due to formate was duplicated to a large degree by pH control with a buffer. It was observed that the uptake of formate from the medium began during early exponential growth and was removed completely before the beginning of stationary phase for both formate and formate plus MOPS flasks. In addition, the formate and the formate plus MOPS flasks did show an enhancement of the production of acetate compared to the control and the control plus MOPS flasks. Despite the higher concentration of acetic acid, the pH of the formate flask did not fall below 6.4. The rate of glucose uptake was identical in the formate, formate plus MOPS, and MOPS flasks which suggests that the increased production of acetate by formate is linked to some step in glucose metabolism and not glucose transport. It appears that the control of pH by formate is due to a symport transport of formate into the cell with the removal of protons from the media. Studies using trimethaprim shown in the Examples suggest that the transported formate requires tetrahydrofolate synthesis to prevent a growth rate slow down.

II. FTAP 1 and 2, PurU and FMD Sequences

The FTAP 1, FTAP 2, PurU and FMD polynucleotides having the sequences as shown in the Figures encode Bacillus subtilis FTAP 1, FTAP 2, PurU and FMD. As will be understood by the skilled artisan, due to the degeneracy of the genetic code, a variety of polynucleotides can encode Bacillus subtilis FTAP 1, FTAP 2, PurU and FMD. The present invention encompasses all such polynucleotides.

The DNA may be obtained by standard procedures known in the art from, for example, cloned DNA (e.g., a DNA "library"), by chemical synthesis, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II) A preferred source is genomic DNA. Nucleic acid sequences derived from genomic DNA may contain regulatory regions in addition to coding regions. Whatever the source, the isolated FTAP 1, FTAP 2, PurU or FMD gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments. are generated, identification of the specific DNA fragment containing the FTAP 1, FTAP 2, PurU or FMD may be accomplished in a number of ways For example, a FTAP 1, FTAP 2, PurU or FMD gene of the present invention or its specific RNA, or a fragment thereof, such as a probe or primer, may be isolated and labeled and then used in hybridization assays to detect a generated FTAP 1, FTAP 2, PurU or FMD gene. (Benton, W. and Davis, R., 1977, Science 196:180; Grunstein, M. And Hogness, D., 1975, Proc. Natl. Acad. Sci. USA 72:3961). Those DNA fragments sharing substantial sequence similarity to the probe will hybridize under stringent conditions.

The present invention encompasses FTAP 1, FTAP 2, PurU and FMD polynucleotide homologs encoding gram-positive microorganism FTAP 1, FTAP 2 PurU and FMD respectively, which have at least 80%, or at least 85%, or at least 90% or at least 95% identity to FTAP 1, FTAP 2, PurU and FMD obtainable from B. subtilis as long as the homolog encodes a protein that retains a functional activity.

Gram-positive microorganism potynucleotide homologs of B. subtilis can be identified through nucleic acid hybridization of gram-positive microorganism nucleic acid of either genomic of cDNA origin. The polynucleotide homolog sequence can be detected by DNA-DNA or DNA-RNA hybridization or amplification using probes, portions or fragments disclosed in the Figures. Accordingly, the present invention provides a method for the detection of B. subtilis FTAP 1, FTAP 2, PurU or FMD polynucleotide homologs which comprises hybridizing part or all of a nucleic acid sequence of B. subtilis FTAP 1, FTAP 2, PurU or FMD with gram-positive microorganism nucleic acid of either genomic or cDNA origin.

Also included within the scope of the present invention are gram-positive microorganism polynucleotide sequences that are capable of hybridizing to the nucleotide sequence of B. subtilis FTAP 1, FTAP 2, PurU or FMD under conditions of intermediate to maximal stringency. Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.) incorporated herein by reference, and confer a defined "stringency" as explained below.

"Maximum stringency" typically occurs at about Tm-5° C. (5° C below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The term "hybridization" as used herein shall include "the process by which a strand of nucleic acid joins with a complementary strand through base pairing" (Coombs J (1994) Dictionary of Biotechnology, Stockton Press, New York N.Y.).

The process of amplification as carried out in polymerase chain reaction (PCR) technologies is described in Dieffenbach C W and G S Dveksler (1995, PCR Primer, a Laboratory Manual, Cold Spring Harbor Press, Plainview N.Y.). A nucleic acid sequence of at least about 10 nucleotides and as many as about 60 nucleotides from B. subtilis FTAP 1, FTAP 2, PurU or FMD preferably about 12 to 30 nucleotides, and more preferably about 20–25 nucleotides can be used as a probe or PCR primer.

The B. subtilis amino acid sequences FTAP 1, FTAP 2, PurU and FMD (shown in FIGS. 1, 2, 3 and 4 respectively) were identified via a FASTA search of Bacillus subtilis genomic nucleic acid sequences. The present invention encompasses gram positive microorganism amino acid variants of B. subtilis FTAP 1, FTAP 2, PurU and FMD that are at least 80% identical, at least 85% identical, at least 90% identical and at least 95% identical to B. subtilis FTAP 1, FTAP 2, PurU and FMD as long as the amino acid sequence variant retains a functional activity.

III. Expression Systems

The present invention provides host cells, expression methods and systems for the enhanced production and secretion of heterologous or homologous proteins in gram-positive microorganisms. In one embodiment, a host cell is genetically engineered to have a deletion or mutation in the gene encoding a gram-positive FTAP 1, FTAP 2, PurU or FMD such that the respective activity is deleted. In another embodiment of the present invention, a gram-positive microorganism is genetically engineered to increase the levels of FTAP 1, FTAP2, Pur2 or FMD, or other molecules associated with formate transport, utilization or cycling.

Inactivation of FTAP 1 or 2 or PurU in a Host Cell

Producing an expression gram-positive microorganism host cell incapable of producing the naturally occurring formate associated protein necessitates the replacement and/or inactivation of the naturally occurring gene from the genome of the host cell. In a preferred embodiment, the mutation is a non-reverting mutation.

One method for mutating nucleic acid encoding a gram-positive formate associated protein is to clone the nucleic acid: or part thereof, modify the nucleic acid by site directed:

mutagenesis and reintroduce the mutated nucleic acid into the cell on a plasmid. By homologous recombination, the mutated gene may be introduced into. the chromosome. In the parent host cell, the result is that the naturally occurring nucleic acid and the mutated nucleic acid are located in tandem on the chromosome. After a second recombination, the modified sequence is left in the chromosome having thereby effectively introduced the mutation into the chromosomal gene for progeny of the parent host cell.

Another method for inactivating the activity is through deleting the chromosomal gene copy. In a preferred embodiment, the entire gene is deleted, the deletion occurring in such as way as to make reversion impossible. In another preferred embodiment, a partial deletion is produced, provided that the nucleic acid sequence left in the chromosome is too short for homologous recombination with a plasmid encoded FTAP 1, FTAP 2, PurU and FMD gene. In another preferred embodiment, nucleic acid encoding the catalytic amino acid residues are deleted.

Deletion of the naturally occurring gram-positive microorganism formate transport, utilization and cycling associated protein can be carried out as follows. A gene encoding a formate associated protein including its 5' and 3' regions is isolated and inserted into a cloning vector. The coding region of the gene is deleted form the vector in vitro, leaving behind a sufficient amount of the 5' and 3' flanking sequences to provide for homologous recombination with the naturally occurring gene in the parent host cell. The vector is then transformed into the gram-positive host cell. The vector integrates into the chromosome via homologous recombination in the flanking regions. This method leads to a gram-positive strain in which the formate associated gene has been deleted.

The vector used in an integration method is preferably a plasmid. A selectable marker may be included to allow for ease of identification of recombinant microorgansims. Additionally, as will be appreciated by one of skill in the art, the vector is preferably one which can be selectively integrated into the chromosome. This can be achieved by introducing an inducible origin of replication, for example, a temperature sensitive origin into the plasmid. By growing the transformants at a temperature to which the origin of replication is sensitive, the replication function of the plasmid is inactivated, thereby providing a means for selection of chromosomal integrants. Integrants may be selected for growth at high temperatures in the presence of the selectable marker, such as an antibiotic. Integration mechanisms are described in WO 88/06623.

Integration by the Campbell-type mechanism can take place in the 5' flanking region of the protease gene, resulting in a protease positive strain carrying the entire plasmid vector in the chromosome in the formate associated protein locus. Since illegitimate recombination will give different results it will be necessary to determine whether the complete gene has been deleted, such as through nucleic acid sequencing,.or restriction maps.

Another method of inactivating the naturally occurring gene is to mutagenize the. chromosomal gene copy by transforming a gram-positive microorganism with oligonucleotides which are mutagenic. Alternatively, the chromosomal gene can be replaced with a mutant gene by homologous recombination.

The present invention encompasses host cells having additional protease deletions or mutations, such as deletions or mutations in apr, npr, epr, mpr and others known to those of skill in the art.

IV. Production of FTAP1, FTAP2, PurU or FMD

For production of FTAP1, FTAP2, PurU or FMD in a host cell, an expression vector comprising at least one copy of nucleic acid encoding a gram-positive microorganism FTAP 1, FTAP 2, PurU or FMD, and preferably comprising multiple copies, is transformed into the host cell under conditions suitable for expression of the protein In accordance with the present invention, polynucleotides which encode a gram-positive microorganism FTAP 1, FTAP 2, PurU FMD or fragments thereof, or fusion proteins or polynucleotide homolog sequences that encode amino acid variants of *B. subtilis* FTAP 1, FTAP 2, PurU or FMD that retain activity may be used to generate recombinant DNA molecules that direct their expression in host cells. In a preferred embodiment, the gram-positive host cell belongs to the genus Bacillus. In another preferred embodiment, the gram positive host cell is *B. subtilis.*

As will be understood by those of skill in the art, it may be advantageous to produce polynucleotide sequences possessing non-naturally occurring codons. Codons preferred by a particular gram-positive host cell (Murray E et al (1989) Nuc Acids Res 17:477–508) can be selected, for example, to increase the rate of expression or to produce recombinant RNA transcripts having desirable properties, such as a longer half-life, than transcripts produced from naturally occurring sequence.

Altered FTAP 1, FTAP 2, PurU or FMD polynucleotide sequences which may be used in accordance with the invention include deletions, insertions or substitutions of different nucteotide residues resulting in a polynucleotide that encodes the same or a functionally equivalent FTAP 1, FTAP 2, PurU or FMD homolog, respectively. As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring protein.

As used herein "substitution" results from the replacement of one or more nucleotides or amino acids by different nucleotides or amino. acids, respectively.

The encoded protein may also show deletions, insertions or substitutions of amino acid residues which produce a silent change and result in a functionally FTAP 1, FTAP 2, PurU or FMD variant. Deliberate amino acid substitutions may be made on the basis of similarity in polarity, charge, solubility, hydrophobicity, hydrophilicity, and/or the amphipathic nature of the residues as long as the variant retains the ability to modulate secretion. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

The FTAP 1, FTAP 2, PurU or FMD polynucleotides of the present invention may be engineered in order to modify the cloning, processing and/or expression of the gene product. For example, mutations may be introduced using techniques which are well known in the art, eg, site-directed mutagenesis to insert new restriction sites, to alter go glycosylation patterns or to change codon preference, for example.

In one embodiment of the present invention, a gram-positive microorganism FTAP 1, FTAP 2, PurU or FMD polynucleotide may be ligated to a heterologous sequence to encode a fusion protein. A fusion protein may also be engineered to contain a cleavage site located between the FTAP1, FTAP2, PurU or FMD nucleotide sequence and the heterologous protein sequence, so that the protein may be cleaved and purified away from the heterologous moiety.

V. Vector Sequences

Expression vectors used in expressing the proteins of the present invention in gram-positive microorganisms comprise at least one promoter associated with a protein selected from the group consisting of FTAP 1, FTAP 2, PurU and FMD, which promoter is functional in the host cell. In one embodiment of the present invention, the promoter is the wild-type promoter for the selected protein and in another embodiment of the present invention, the promoter is heterologous to the protein, but still functional in the host cell. In one preferred embodiment of the present invention, nucleic acid encoding the protein is stably integrated or otherwise stably maintained in the microorganism genome.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the gram-positive host which allows for ease of selection of those hosts containing the vector. Examples of such selectable markers include but:are not limited to antibiotics, such as, erythromycin, actinomycin, chloramphenicol and tetracycline.

VI. Transformation

A variety of host cells can be used for the production of FTAP 1, FTAP 2, PurU and FMD including bacterial, fungal, mammalian and insects cells. General transformation procedures are taught in Current Protocols In Molecular Biology vol. 1, edited by Ausubel et al., John Wiley & Sons, Inc. 1987, chapter 9 and include calcium phosphate methods, transformation using DEAE-Dextran and electroporation. Plant transformation methods are taught in Rodriquez (WO 95/14099, published May 26, 1995).

In a preferred embodiment, the host cell is a gram-positive microorganism and in another preferred embodiment, the host cell is Bacillus. In one embodiment of the present invention, nucleic acid encoding one or more proteins of the present invention is introduced into a host cell via an expression vector capable of replicating within the Bacillus host cell. Suitable replicating plasmids for Bacillus are described in Molecular Biological Methods for Bacillus, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, nucleic acid encoding a protein of the present invention is stably integrated into the microorganism genome. Preferred host cells are gram-positive host cells. Another preferred host is Bacillus. Another preferred host is *Bacillus subtilis*. Several strategies have been described in the literature for the direct cloning of DNA in Bacillus. Plasmid marker rescue transformation involves the uptake of a donor plasmid by competent cells carrying a partially homologous resident plasmid (Contente et al., Plasmid 2:555–571 (1979); Haima et al., Mol. Gen. Genet. 223:185–191 (1990); Weinrauch et al., J. Bacteriol. 154(3):1077–1087 (1983); and Weinrauch et al., J. Bacteriol. 169(3):1205–1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979) Mol. Gen. Genet 168:111–115; for *B. megaterium* in Vorobjeva et al., (1980) FEMS Microbiol. Letters 7:261–263; for *B. amyloliquefaciens* in Smith et al., (1986) Appl. and Env. Microbiol. 51:634; for *B. thuringiensis* in Fisher et al., (1981) Arch. Microbiol. 139:213–217; for *B. sphaericus* in McDonald (1984) J. Gen. Microbiol. 130:203; and *B. larvae* in Bakhiet et al., (1985) 49:577. Mann et al., (1986, Current Microbiol. 13:131–135) report on transformation of Bacillus protoplasts and Holubova, (1985) Folia Microbiol. 30:97) disclose methods for introducing DNA into protoplasts using DNA containing liposomes.

VII. Identification of Transformants

Whether a host cell has been transformed with a mutated or a naturally occurring gene encoding a gram-positive FTAP 1, FTAP 2, PurU or FMD, detection of the presence/absence of marker gene expression can suggests whether the gene of interest is present However, its expression should be confirmed. For example, if the nucleic acid encoding a FTAP1, FTAP2, PurU or FMD is inserted within a marker gene sequence, recombinant cells containing the insert can be identified by the absence of marker gene function. Alternatively, a marker gene can be placed in tandem with nucleic acid encoding the FTAP1, FTAP2, PurU or FMD under the control of a single promoter. Expression of the marker gene in response to induction or selection usually indicates expression of the FTAP 1, FTAP 2, PurU and FMD as well.

Alternatively, host cells which contain the coding sequence for a FTAP 1, FTAP 2, PurU and FMD and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the polynucleotide sequence can be detected by DNA-DNA or DNA-RNA hybridization or amplification using probes, portions or fragments of *B. subtilis* FTAP 1, FTAP 2, PurU or FMD.

VIII. Secretion of Recombinant Proteins

Means for determining the levels of secretion of a heterologous or homologous protein in a gram-positive host cell and detecting secreted proteins include, using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton R et al (1990, Serological Methods, a Laboratory Manual, APS Press, St Paul Minn.) and Maddox D E et al (1983, J Exp Med 158:1211).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 and incorporated herein by reference.

IX. Purification of Proteins

Gram positive host cells transformed with polynucleotide sequences encoding heterologous or homologous protein may be cultured under conditions suitable for the expression and recovery of the encoded protein from cell culture. The protein produced by a recombinant gram-positive host cell comprising a FTAP 1, FTAP 2, PurU and FMD of the present invention will be secreted into the culture media. Other recombinant constructions may join the heterologous or homologous polynucleotide sequences to nucleotide sequence encoding a polypeptide domain which will facilitate purification of soluble proteins (Kroll D J et al (1993) DNA Cell Biol 12:441–53).

Such purification facilitating domains include, but are not limited to, metal chelating peptides such as histidine-tryptophan modules that allow purification on immobilized metals (Porath J (1992) Protein Expr Purif 3:263–281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification.

X. Uses of The Present Invention

FTAP 1, FTAP 2, PurU and FMD and Genetically Engineered Host Cells

The present invention provides genetically engineered gram-positive microorganisms comprising preferably non-revertable mutations or deletions in the naturally occurring gene encoding FTAP 1, FTAP 2, PurU or FMD such that activity is diminished or deleted altogether.

In another embodiment, the microorganism is further genetically engineered to produce a recombinant protein or polypeptide. In a preferred embodiment the host cell is a Bacillus. In another preferred embodiment, the host cell is a Bacillus subtilis.

In an alternative embodiment, a host cell is genetically engineered to produce a gram-positive FTAP 1, FTAP 2, PurU or FMD. In a preferred embodiment, the host cell is grown under large scale fermentation conditions, the FTAP 1, FTAP 2, PurU or FMD is isolated and/or purified.

FTAP 1, FTAP 2. PurU and FMD Polynucleotides

A *B. subtliis* FTAP1, FTAP2, PurU or FMD polynucleotide, or any part thereof, provides the basis for detecting the presence of gram-positive microorganism polynucleotide homologs through hybridization techniques and PCR technology.

Accordingly, one aspect of the present invention is to provide for nucleic acid hybridization and PCR probes which can be used to detect polynucleotide sequences, including genomic and cDNA sequences, encoding gram-positive FTAP 1, FTAP 2, PurU or FMD or portions thereof.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

EXAMPLES

Materials and Methods

Bacterial Strains and Media

The *Bacillus subtilis* strain used was a derivative of I168 called BG125 (hisA1 thr5 trpC2) provided by J. A. Hoch. The strain was grown on Luria-Bertani agar (LA. 1% SBG medium contained the following: soytone; Difco, 10 g/L, glucose; Sigma, 10 g/L, yeast extract; Difco, 5 g/L, NaCl, Norton, 10 g/L, pH 7.0. 1% SBG plus MOPS, Sigma, contained 80 mM MOPS pH 7.0. Sodium formate, EM Science, at various concentrations was added to 1% SBG where indicated. The pH of all media was adjusted to 7 with NaOH. The growth medium for the bactericidal tests of formate was SBG1 % supplemented with 50 mM MES, Sigma, 50 mM HEPES, Sigma, followed by pH adjustment to the pH value indicated with either NaOH or HCL. Formic acid was then added to a final concentration of 50 mM which resulted in no change in the pH of the growth medium. MM294 competent cells (Ausubel et al. 1992, Short Protocols in Molecular Biology. John Wiley and Sons, New York) were used for plasmid construction and propagation. LB broth and agar were used for growing MM294 cells and were supplemented with 50 ug/ml carbenicillin for selection. BG125 was grown on LB agar or in LB liquid medium supplemented with 10 $\mu$g/ml of kanamycin for selection.

Trimethaprim was dissolved in 50% ethanol and added to a final concentration of 50 ug/ml where indicated when the growth had reached a Klett reading between 20–30 units. The additions for trimethaprim experiments were added at the following final concentrations: 10 ug/ml glycine, 10 ug/ml methionine, 50 ug/ml thymidine, 20 ug/ml adenosine, and 20 ug/ml guanosine.

DNA Manipulations

Chromosomal DNA extraction, plasmid DNA extraction, PCR clean-up and DNA fragment extraction from gels were performed using the QIAGEN Blood & Cell Culture DNA Kit, QIAprep Spin Miniprep Kit, QIAquick™ PCR Purification Kit and the QIAquick™ Gel Extraction Kit respectively. Enzymatic amplification of DNA by PCR was according to standard protocol. Restriction endonuclease digestion and ligation of DNA were performed as specified by the manufacturers. The DNA sequence identity search for yrhG FTAP 1) and ywcJ (FTAP 2) was performed using the GCG software package (Genetics Computer Group).

Plasmid Construction

The cloning vector used in this study was pUC/Ts/Kan, an *E. coli-B. subtilis* shuttle vector. The plasmid consists of the pUC19 plasmid, the temperature sensitive origin of replication from the *Staphylcoccus aureus* plasmid derivative pE194Ts (Fleming et al. 1995, App. Env. Microb. 61:3775–3780), and the kanamycin gene from *Streptococcus faecalis* (Trieu-Cuot et al. 1983, Gene 23: 331–341).

A 0.438-Kb DNA segment of the yrhG gene was amplified from *B. subtilis* BG125 chromosomal DNA by PCR using Taq DNA polymerase (Boehringer Mannheim), and oligonucleotide primers GCGCGC GGATCCGTAATTGGCGATCTTCCGAAAGAATGG (SEQ ID NO: 11) and GCGCGC CTGCAGGGGAACCAGATGCCAAGGATTTTTCC (SEQ ID NO: 12) (the BamHI and PstI sites are underlined). The PCR product was digested with BamHI and PstI and ligated with the 5.3-Kb BamHI-PstI fragment from plasmid pUC/Ts/Kan to construct the yrhG-homologue interruption plasmid pTRANS1. Plasmid pTRANS2 was constructed in a similar way by amplifying a 0.543-Kb DNA of the ywcJ gene using Taq DNA polymerase and oligonucleotide primers GCGCGC GGATCCTTGGTTTTGGCATTACAGCCGC (SEQ ID: 13) and GCGCGC CTGCAGAGGGTGCTCGATCAAAAGCGAGATGG (SEQ ID NO: 14) (the BamHI and PstI sites are underlined). The PCR product was digested with BamHI and PstI and ligated with the 5.3-Kb BamHI-PstI fragment from plasmid pUC/Ts/Kan to construct the ywcJ-homologue interruption plasmid. DNA sequencing was performed on. both the pTRANS1 and pTRANS2 interuption plasmids to verify the presence of the correct PCR generated fragment using an Applied Biosystems 373A DNA sequencer. The sequencing primers used were the mp19/pUC19 24-mer reverse sequencing primer and the mp19/pUC19 24-mer sequencing primer from New England Biolabs.

Introduction of the Gene Interruptions into *B. subtilis*.

To construct *B. subtilis* strains containing an interruption of either the yrhG or ywcJ genes, pTRANS1 and pTRANS2 were transformed separately into BG125 by protoplast transformation as described (Chang et al. 1979, Mol. Gen. Genet. 168:111–115) and plated on protoplast regeneration medium with 200 ug/ml kanamycin at 30° C. Resulting kanamycin resistant transformants were grown overnight in LB liquid medium containing kanamycin at 45° C. Integrants were plated and then colony purified on LB plates containing kanamycin at 45° C. Isolated colonies were then frozen in LB liquid medium plus 30% glycerol at −70° C. for preservation.

Growth Conditions.

Prior to shake flask experiments BG125 was grown from frozen stocks onto LB agar and grown overnight at 37° C. Cells were removed from the plates to 6 mls of SBG1% in test-tubes and grown at 37° C. for three hours. 0.2 mls of the seed culture was used to inoculate a pre-warmed 300 ml nephlometer flask containing 20 mls of the appropriate media. Flasks were incubated at 37° C. (except where indicated) and 300 rpm in a New Brunswick Scientific Shaker. At the indicated time points, the amount of cell growth was determined by a Klett-Summerson Photoelectric Colorimeter, the pH of the flask was taken using a Corning pH/iometer, and 1.25 mls was removed for further processing. The sample was spun in an eppendorf microfuge and 1 ml of supernatant was removed and mixed with 30 μls of perchloric acid HPLC analysis. The remaining supernatant was saved for glucose analysis. All samples were stored at −70° C. until analysis. Medium pH titrations were performed by the stepwise addition of HCl followed by pH measurement. The bactericidal tests of pH and formate on *B. subtilis* were carried out by growing BG125 as described above in SBG1% to a density of $5\times10^6$ cfu/ml. The cells were then adjusted to a concentration of $5\times10^4$ cfu/ml with buffered SBG1% adjusted to the pH indicated, with and without 50 mM formate. Cultures were then incubated at 37° C. with shaking for 3 hours. Samples were taken at 0, 1 2 and 3 hours, serially diluted and plated to LB at 37° C. for determination of cell viability.

Analysis of Metabolic By-products.

One ml of acid treated culture supernatant was filtered through a 0.2 μm membrane filter. The concentrations of the metabolic by-products was determined with high performance liquid chromatography (HPLC). A Shodex SH1011 cation-exchange column heated to 50° C. was used. The solvent used was 5 mM sulfuric. acid ($H_2SO_4$) at a flow rate of 0.4 ml./min. The HPLC system consisted of a Waters model 510 pump with a pulse dampener SSI model LP-21, an Refractive Index (RI) detector Waters 410 Differential Refactometer model, a Waters autoinjector 712 WISP model injecting 20 μL injections per sample. The HPLC was interfaced with a Millennium 2.15.01 HPLC control system for s mobile phase flow control, integration, and data collection and storage. To identify different peaks, standards were run and compared to the peaks in the samples. The standards run were: acetoin, acetic acid, 2,3-butanediol, butyric acid, citric acid, formic acid, ethanol, fumaric acid, malic acid, glycerol, lactic acid, propionic acid, and pyruvic acid all from Sigma.

Example I

Example I illustrates that formate addition increases growth by pH control.

BG125 was grown as described in Materials and Methods. In 1% SBG (pH 7) medium with and without 3 g/l (44 mM) sodium formate, the addition of sodium formate resulted in more total growth compared to the control flask and it also acted to prevent the fall of shake flask pH below 6.5 while the control flask pH dropped to 5.5 (FIG. 5). With a pKa of 3.73, formate should have little buffering activity at a starting pH of 7. To rule out any buffer effects of our media, a pH titration experiment was performed with 1% SBG, and 1% SBG containing either 3 g/l sodium formate or 80 mM MOPS. FIG. 6 shows that in 1% SBG, and 1% SBG with sodium formate there is little buffering activity down to pH 5.0. 1% SBG medium containing MOPS (pKa 7.20) showed buffering activity in the expected range. When BG 125 was grown in SBG1% containing 80 mM MOPS which prevented a pH drop below 6.3, the growth of the strain was near the levels of the formate containing flask (FIG. 5). In addition, a flask containing MOPS plus formate grew almost identically to the MOPS flask (FIG. 5).

Example II

Example II illustrates that increasing concentrations of formate cause a lag in initial growth rate.

When using 3 g/l mN sodium formate, a slight lag in the initial growth rate was observed. To further investigate this lag, the growth of BG125 with higher concentrations of sodium formate (up to 21 g/l) was tested. It was found that there was a correlation between increasing concentrations of formate and the duration of the initial lag period (FIG. 7). All the cultures tested did resume growth after the lag period at similar rates and reached higher densities than the control flask.

Example III

Example III illustrates that formate addition results in increased acetate production.

To further study the effect of formate on growth of BG125 we also studied the production of various organic by-products and the utilization of glucose in the shake flasks of FIG. 5. FIG. 8 shows that the uptake of formate from the medium began during early exponential growth and was removed completely before the beginning of stationary phase for both the formate and formate plus MOPS flasks (FIG. 5). Measurement of acetate levels (FIG. 9) revealed the production of large amounts of this compound in all flasks which is likely the cause of the drop in pH during growth in SBG1%; however, the amounts of acetate produced did vary. The control flask, 1% SBG only, slowed the production of acetate first, and reached about 1.5 g/L. The flask buffered with MOPS reached close to 2 g/L of acetate at a faster rate than the control. The two flasks containing formate continued to produce acetate for the longest period and reached between 2.5 and 3 g/L.

Example IV

Example IV illustrates that glucose uptake was not enhanced by formate.

When glucose levels were examined during the experiment (FIG. 10) the MOPS, formate, and MOPS plus formate flasks used glucose at the same rate until it was undetectable by 450 minutes. The control flask utilized glucose at the same rate until 250 minutes when the uptake slowed down and stopped at 6 g/L.

Example V

Example V shows that trimethaprim addition slows growth in the presence of formate.

To study the effect of trimethaprim, a tetrahydrofolate synthesis inhibitor, we performed an experiment where we added trimethaprim to flasks containing SBG1%, SBG1% plus formate plus growth additives and a control containing SBG1% plus growth additives. The effect of ethanol used to dissolve the trimethaprim was also tested. FIG. 11 shows that the addition of trimethaprim had an inhibitory effect on the growth of B. subtilis in SBG1% medium compared to growth in SBG1% alone. The addition of additives to supplement pathways dependent on tetrahydrofolate to a flask containing trimethaprim partially restored the growth of the strain. When formate was added to a flask containing trimethaprim and the growth enhancing additives, the rate of growth was then significantly reduced, but still above that of the flask with trimethaprim alone. Ethanol did not have any effect on growth.

Example VI

Formate Enhances the Bactericidal Effect of Low pH on B. subtilis Cultures

In order to determine if any of the observed effects of formate at pH 7.0 such as the B. subtilis growth lag involved lethal toxicity to a portion of the cell population, we examined the effect of formate on cell viability at a culture pH of 7 and lower. With a $pK_a$ of 3.75, we expected formate to be toxic near this pH. Cultures of BG125 were inoculated into buffered SBG1% with and without 50 mM formate at pH 3.6, 4.0, 4.6 and 7.0. The results showed that the cultures with and without formate lost complete viability within two hours of incubation at pH 3.6. After one hour at pH 3.6, the percent of survivors based on the initial titer was 1.8 % while the addition of formate consistently decreased the percent survivors to an average of 0.13%. Incubation at pH 4.0 without formate resulted in a lower loss of viability than pH 3.6, reaching 38 % survivors by 3 hours of incubation. Formate increased the loss of viability at pH 4.0 down to 1.2% survivors by 3 hours. Cultures incubated at pH 4.6 showed no decline in viability with or with out formate. Incubation at pH 7.0 also showed no decline of viability and a increase of cell count suggests that some growth was taking place as expected for this concentration of formate.

These results suggest that a gram-positive microorganism fermentation will need to be pH controlled and should not fall below pH 4.6 if formic acid is produced during the culture.

Example VII

Homologues to FTAP 1 and FTAP 2

Homologues to FTAP 1 (YrhG) and FTAP 2 (YwcJ) are shown in Tables. 1A and 1B. All the homologues found indicated that YrhG and YwcJ are related to proteins involved in transport of formate or other small molecules. YrhG and YwcJ are predicted to be hydrophobic proteins of similar size bearing multiple transmembrane regions.

Example VIII

Example VIII illustrates the effect that an interruption of the gene encoding FTAP 1 or FTAP 2 had on the growth of Bacillus cells, illustrated in FIGS. 16 and 17, respectively.

For both genes, PCR primers were constructed to amplify an internal region of the genes for gene interruption. These internal fragments were cloned into a replicating plasmid with a temperature sensitive origin of replication for Bacillus. When transformed into the B. subtilis test strain, the plasmid was maintained by antibiotic selection of plasmid markers.

Upon temperature upshift in the presence of antibiotic, clones were obtained in which the plasmid has integrated via the region of homology into the chromosome of the Bacillus. This resulted in the interruption of the genes being tested which was maintained by growing the cells above the replication origin activity temperature in the presence of antibiotic. The integrants were tested in shake flasks containing 1% SBG, antibiotic, and with and with out formate. The presence of antibiotic alone on the integrants was tested and had no effect on growth. The integrants were tested against control flasks containing the strain without the plasmids.

The results showed that the interruption of each genes had an effect on growth only when formate was added. The interruption of YrhG reduced the normal growth enhancement effect of formate by half. These could be explained by a decrease in the uptake of formate due to the interruption. The interruption of YwcJ (FTAP 2)resulted in a toxic effect which caused a decline of growth well below growth of the control strain with out formate. It thus appears that each gene has a role in formate transport or utilization.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

TABLE 1A

Amino Acid sequence identities between YrhG and YwcJ proteins with related polypeptides

Identity with the YrhG protein

| Features | no. of residues overlap) | E. coli | B. subtilis | S. typh. [a] | Methano. [b] | H. infl. [c] | Yeast | Ref. |
|---|---|---|---|---|---|---|---|---|
| Hypothetical 70 KD protein | 262 | | | | | | YHA8, 31.7 | 1994 Science 265:2077 |
| Potential formate transporter | 268 | | | | FdhC, 47.0 | | | 1992 J. Bacteriol. 174: 4997 |
| Formate dehydrogenase | 271 | | | | FdhC, 45.4 | | | 1997 J. Bacteriol. 179: 899 |
| Probable formate transporter | 275 | | | | | FocA, 31.3 | | 1995 Science 269: 496 |
| Potential nitrite transporter | 254 | NirC, 31.1 | | | | | | 1990 Eur. J. Biochem. 191:315 |
| Potential nitrite transporter | 239 | | | NirC, 31.8 | | | | 1991 J. Bacteriol. 173: 325 |
| Probable formate transporter 1 | 276 | FocA, 34.1 | | | | | | 1989 J. Bacteriol. 171: 2485 |
| Probable formate transporter 2 | 269 | FocB, 33.1 | | | | | | 1997 Microbiol. 143:3633 |
| Hypothetical 28.4 KD protein | 233 | | YweJ, 27 | | | | | 1997, Nature. 390:249 |

[a] Salmonella thyphimuriun
[b] Methanobacteria
[c] Haemophilus influenzae

TABLE 1B

Identity with the JwcJ protein

| Features | no. of residues overlap) | E. coli | B. subtilis | S. typh. [a] | Methano. [b] | H. infl. [c] | Yeast | Ref. |
|---|---|---|---|---|---|---|---|---|
| Hypothetical 70 KD protein | 238 | | | | | | YHA8, 26.1 | 1994 Science 265:2077 |
| Potential formate transporter | 243 | | | | FdhC, 27.2 | | | 1992 J. Bacteriol. 174: 4997 |
| Formate dehydrogenase | 247 | | | | FdhC, 29.6 | | | 1997 J. Bacteriol. 179: 899 |
| Probable formate transporter | 234 | | | | | FocA, 27.4 | | 1995 Science 269: 496 |
| Potential nitrite transporter | 256 | NirC, 35.2 | | | | | | 1990 Eur. J. Biochem. 191:315 |
| Potential nitrite transporter | 256 | | | NirC, 34.4 | | | | 1991 J. Bacteriol. 173: 325 |
| Probable formate transporter 1 | 294 | FocB, 27.8 | | | | | | 1997 Microbiol. 143:3633 |
| Probable formate transporter 2 | 282 | FocA, 29.4 | | | | | | 1989 J. Bacteriol. 171: 2485 |
| Formate dehydrogenase | 233 | | YrhG, 27 | | | | | 1997, Nature. 390:249 |

All values are percentage sequence identity.
[a] Salmonella thyphimuriun
[b] Methanobacteria
[c] Haemophilus influenzae

What is claimed is:

1. A method for producing a product in a gram-positive microorganism comprising:
   a) obtaining a gram-positive microorganism capable of producing the product; and
   b) culturing said microorganism in the presence of formate and under conditions suitable for production of said product,
wherein said gram-positive microorganism is transformed with an introduced polynucleotide sequence selected from the group consisting of SEQ ID NO: 1, SEQ ID NO: 3, and a polynucleotide sequence having at least 85% identity to SEQ ID NO: 1 or, SEQ ID NO: 3 wherein said polynucleotide sequence encodes a formate transporter associated protein (FTAP).

2. The method of claim 1 wherein said product is a recombinant protein.

3. The method of claim 2 wherein said recombinant protein is homologous to said microorganism.

4. The method of claim 2 wherein said recombinant protein is heterologous to said microorganism.

5. The method of claim 1 wherein said gram-positive microorganism is from the genus Bacillus.

6. The method of claim 5 wherein said Bacillus is selected from the group consisting of B. subtilis, B. licheniformis, B. lentus, B. brevis, B. stearothermophilus, B. alkalophilus, B. amylohquefaciens, B. coagulans, B. circulans, B. lautus and B. thuringiensis.

7. The method of claim 2 wherein said recombinant protein is selected from the group consisting of protein hormones, enzymes, growth factors and protein cytokines.

8. The method of claim 7 wherein said recombinant protein is an enzyme.

9. The method of claim 8 wherein said enzyme is selected from the group consisting of proteases, lipases, amylases, and pullulanases.

10. The method of claim 1 wherein said formate transport associated protein (FTAP) is FTAP 1 having the amino acid sequence of SEQ ID NO: 4.

11. The method of claim 1 wherein said formate transport associated protein (FTAP) is FTAP 2 having the amino acid sequence of SEQ ID NO: 4.

12. The method of claim 1 wherein said formate transport associated protein has an amino acid sequence at least 95% identical to the amino acid sequence set forth in SEQ ID NO: 2.

13. The method of claim 1 wherein said formate transport associated protein has an amino acid sequence at least 95% identical to the amino acid sequence set forth in SEQ ID NO: 4.

14. The method of claim 8 wherein said enzyme is selected from the group consisting of glucose isomerase, laccase and protein disulfide isomerase.

15. The method of claim 8 wherein said enzyme is cellulase.

16. A method of producing a protein in a Bacillus host cell comprising the steps of:
   a) transforming a Bacillus host cell with a polynucleotide sequence encoding a formate transport associated protein having an amino acid sequence selected from the group consisting of SEQ ID NO: 2, SEQ ID NO: 4 and a sequence at least 90% identical to SEQ ID NO: 2 or SEQ ID NO: 4; and
   b) culturing said Bacillus host cell in the presence of formate under conditions suitable for the production of said protein.

17. The method according to claim 16 further comprising the step of recovering said protein from the cell culture.

18. The method according to claim 17, wherein said protein is a recombinant heterologous protein.

19. The method according to claim 17 wherein said protein is a recombinant, homologous protein.

* * * * *